US011033394B2

(12) United States Patent
Hamzey et al.

(10) Patent No.: US 11,033,394 B2
(45) Date of Patent: Jun. 15, 2021

(54) IMPLANT WITH MULTI-LAYER BONE INTERFACING LATTICE

(71) Applicant: Institute for Musculoskeletal Science and Education, Ltd., King of Prussia, PA (US)

(72) Inventors: Rami Hamzey, Philadelphia, PA (US); Robert Morris, Gwynedd Valley, PA (US); William Duffield, Collegeville, PA (US); Mathew Gordon, Collegeville, PA (US); Edward J. McShane, III, Collegeville, PA (US); Joseph M. Nyahay, Eagleville, PA (US)

(73) Assignee: INSTITUTE FOR MUSCULOSKELETAL SCIENCE AND EDUCATION, LTD., King of Prussia, PA (US)

( * ) Notice: Subject to any disclaimer, the term of this patent is extended or adjusted under 35 U.S.C. 154(b) by 0 days.

(21) Appl. No.: 15/791,232

(22) Filed: Oct. 23, 2017

(65) Prior Publication Data
US 2018/0296350 A1    Oct. 18, 2018

Related U.S. Application Data

(60) Provisional application No. 62/412,657, filed on Oct. 25, 2016.

(51) Int. Cl.
*A61F 2/30*    (2006.01)
*A61F 2/44*    (2006.01)
(Continued)

(52) U.S. Cl.
CPC .......... *A61F 2/30907* (2013.01); *A61B 17/56* (2013.01); *A61B 17/72* (2013.01);
(Continued)

(58) Field of Classification Search
CPC ................ A61F 2/28; A61F 2002/2835; A61F 2002/30331; A61F 2310/00359;
(Continued)

(56) References Cited

U.S. PATENT DOCUMENTS 4,280,233 A * 7/1981 Raab ........................ A61F 2/00
                                                                 428/170
4,542,539 A    9/1985 Rowe, Jr. et al.
(Continued)

FOREIGN PATENT DOCUMENTS

CN    101708138 A    5/2010
DE    19722389 A1    12/1998
(Continued)

OTHER PUBLICATIONS

International Search Report and Written Opinion dated Jan. 30, 2018 for International Patent Application No. PCT/2017/58018.
(Continued)

*Primary Examiner* — Ann Schillinger
(74) *Attorney, Agent, or Firm* — Plumsea Law Group, LLC

(57) ABSTRACT

An implant includes a body including a substrate and a bone interfacing lattice disposed on the substrate. The bone interfacing lattice includes at least two layers of elongate curved structural members. In addition, the at least two layers of elongate curved structural members include a first layer adjacent the substrate and a second layer adjacent the first layer. Also, the first layer has a first deformability and the second layer has a second deformability, wherein the second deformability is greater than the first deformability.

12 Claims, 23 Drawing Sheets

(51) Int. Cl.
  *A61F 2/36* (2006.01)
  *A61F 2/38* (2006.01)
  *A61F 2/40* (2006.01)
  *A61F 2/28* (2006.01)
  *A61F 2/42* (2006.01)
  *A61B 17/56* (2006.01)
  *A61B 17/72* (2006.01)
  *A61F 2/34* (2006.01)
  *A61B 17/00* (2006.01)

(52) U.S. Cl.
  CPC ...... *A61B 17/7208* (2013.01); *A61B 17/7291* (2013.01); *A61F 2/28* (2013.01); *A61F 2/30734* (2013.01); *A61F 2/3662* (2013.01); *A61F 2/389* (2013.01); *A61F 2/4081* (2013.01); *A61F 2/4202* (2013.01); *A61B 2017/00893* (2013.01); *A61F 2002/30006* (2013.01); *A61F 2002/3007* (2013.01); *A61F 2002/30014* (2013.01); *A61F 2002/3093* (2013.01); *A61F 2002/30235* (2013.01); *A61F 2002/30289* (2013.01); *A61F 2002/30451* (2013.01); *A61F 2002/30604* (2013.01); *A61F 2002/30738* (2013.01); *A61F 2002/30805* (2013.01); *A61F 2002/30878* (2013.01); *A61F 2002/30891* (2013.01); *A61F 2002/30914* (2013.01); *A61F 2002/30919* (2013.01); *A61F 2002/30929* (2013.01); *A61F 2002/30985* (2013.01); *A61F 2002/3425* (2013.01); *A61F 2002/3863* (2013.01); *A61F 2002/4029* (2013.01); *A61F 2002/4205* (2013.01); *A61F 2002/4207* (2013.01); *A61F 2002/4228* (2013.01)

(58) Field of Classification Search
  CPC ...... A61F 2/442; A61F 2/4455; A61F 2/4611; A61F 2002/30013; A61F 2002/3092; A61F 2002/3093; A61F 2002/30985; A61F 2/2846; A61F 2/30907; A61F 2002/30622
  See application file for complete search history.

(56) References Cited

U.S. PATENT DOCUMENTS

| | | | |
|---|---|---|---|
| 4,955,911 A * | 9/1990 | Frey | A61F 2/28 623/23.51 |
| 5,198,308 A | 3/1993 | Shetty et al. | |
| 5,496,372 A * | 3/1996 | Hamamoto | A61L 27/56 623/23.54 |
| D403,069 S | 12/1998 | Drewry et al. | |
| 5,973,222 A | 10/1999 | Devanathan et al. | |
| 7,527,649 B1 | 5/2009 | Blain | |
| 8,062,365 B2 | 11/2011 | Schwab | |
| 8,430,930 B2 | 4/2013 | Hunt | |
| 8,568,413 B2 | 10/2013 | Mazur et al. | |
| 9,220,518 B2 | 12/2015 | Neal et al. | |
| 9,237,958 B2 | 1/2016 | Duggal et al. | |
| 9,364,330 B2 | 6/2016 | Lindsey et al. | |
| 9,421,108 B2 | 8/2016 | Hunt | |
| 9,433,510 B2 | 9/2016 | Lechmann et al. | |
| 9,433,511 B2 | 9/2016 | Bagga et al. | |
| 9,439,779 B2 | 9/2016 | Zhang et al. | |
| 9,452,056 B2 | 9/2016 | Early et al. | |
| 9,452,064 B2 | 9/2016 | Trautwein et al. | |
| 9,456,901 B2 | 10/2016 | Jones et al. | |
| 9,456,907 B1 | 10/2016 | Castro | |
| 9,545,317 B2 | 1/2017 | Hunt | |
| 9,549,823 B2 | 1/2017 | Hunt et al. | |
| 9,554,914 B2 | 1/2017 | Taylor et al. | |
| 9,561,117 B2 | 2/2017 | Lechmann et al. | |
| 9,572,669 B2 | 2/2017 | Hunt et al. | |
| 9,597,197 B2 | 3/2017 | Lechmann et al. | |
| 9,622,880 B2 | 4/2017 | Dunworth et al. | |
| 9,636,226 B2 | 5/2017 | Hunt | |
| 9,649,200 B2 | 5/2017 | Wickham | |
| 9,662,157 B2 | 5/2017 | Schneider et al. | |
| 9,662,224 B2 | 5/2017 | Weiman et al. | |
| 9,662,226 B2 | 5/2017 | Wickham | |
| 9,744,051 B2 | 8/2017 | Biedermann et al. | |
| 9,757,235 B2 | 9/2017 | Hunt et al. | |
| 9,782,270 B2 | 10/2017 | Wickham | |
| 9,788,967 B2 | 10/2017 | Jo | |
| 9,814,578 B1 | 11/2017 | Gotfried | |
| 9,918,849 B2 | 3/2018 | Morris et al. | |
| 9,931,209 B2 | 4/2018 | Gotfried | |
| 9,987,051 B2 | 6/2018 | Nunley et al. | |
| 9,987,137 B2 | 6/2018 | Hunt et al. | |
| 9,999,516 B2 | 6/2018 | Hunt | |
| 10,004,546 B2 | 6/2018 | Gotfried | |
| 10,016,279 B1 | 7/2018 | Castro | |
| 10,058,433 B2 | 8/2018 | Lechmann et al. | |
| 10,064,737 B2 | 9/2018 | Tsai et al. | |
| 10,098,754 B2 | 10/2018 | Larsson | |
| 10,117,746 B2 | 11/2018 | Cordaro | |
| 10,143,569 B2 | 12/2018 | Weiman et al. | |
| 10,154,913 B2 | 12/2018 | Steinmann et al. | |
| 10,194,962 B2 | 2/2019 | Schneider et al. | |
| 10,195,524 B2 | 2/2019 | DeRidder et al. | |
| 10,213,317 B2 | 2/2019 | Bishop et al. | |
| 10,226,357 B2 | 3/2019 | Ries | |
| 10,271,958 B2 | 4/2019 | Schaufler et al. | |
| 10,278,833 B2 | 5/2019 | Howard et al. | |
| 10,278,834 B2 | 5/2019 | Howard et al. | |
| 10,357,377 B2 | 7/2019 | Nyahay et al. | |
| 10,369,009 B2 | 8/2019 | Joly et al. | |
| 10,413,427 B2 | 9/2019 | Trieu | |
| 10,433,977 B2 | 10/2019 | Lechmann et al. | |
| 10,433,979 B2 | 10/2019 | Morris et al. | |
| 10,449,051 B2 | 10/2019 | Hamzey et al. | |
| 10,449,055 B2 | 10/2019 | McJunkin | |
| 10,449,058 B2 | 10/2019 | Lechmann et al. | |
| 10,478,312 B2 | 11/2019 | McShane, III et al. | |
| 10,492,921 B2 | 12/2019 | McShane, III et al. | |
| 10,507,118 B2 | 12/2019 | Afzal | |
| 10,512,549 B2 | 12/2019 | Bishop et al. | |
| 10,517,739 B2 | 12/2019 | Ryan | |
| 10,524,926 B2 | 1/2020 | Jasinski | |
| 10,524,927 B2 | 1/2020 | Ryan | |
| 10,524,929 B2 | 1/2020 | Shoshtaev | |
| 10,525,688 B2 | 1/2020 | O'Neill et al. | |
| 10,531,962 B2 | 1/2020 | Petersheim et al. | |
| 10,555,819 B2 | 2/2020 | Miccio | |
| 10,561,456 B2 | 2/2020 | Cawley et al. | |
| 10,575,965 B2 | 3/2020 | Kim et al. | |
| 10,588,755 B2 | 3/2020 | Vogt et al. | |
| 10,617,532 B2 | 4/2020 | Mazur et al. | |
| 10,624,760 B2 | 4/2020 | Mirda et al. | |
| 10,660,763 B2 | 5/2020 | Wilson et al. | |
| 10,660,764 B2 | 5/2020 | Maglaras et al. | |
| 10,667,924 B2 | 6/2020 | Nyahay et al. | |
| 10,675,158 B2 | 6/2020 | Unger et al. | |
| 10,682,238 B2 | 6/2020 | Petersheim et al. | |
| 10,695,192 B2 | 6/2020 | Bishop et al. | |
| 10,709,570 B2 | 7/2020 | Stauffer et al. | |
| 10,716,678 B2 | 7/2020 | Stampfli et al. | |
| 10,722,378 B2 | 7/2020 | Davis et al. | |
| 10,744,001 B2 | 8/2020 | Sack | |
| 10,744,003 B2 | 8/2020 | Ryan et al. | |
| 10,765,530 B2 | 9/2020 | Steinmann et al. | |
| 10,772,732 B1 | 9/2020 | Miller et al. | |
| 10,849,756 B2 | 12/2020 | Hunt et al. | |
| 10,856,999 B2 | 12/2020 | Bishop et al. | |
| 2007/0179610 A1 * | 8/2007 | Biedermann | A61F 2/4465 623/16.11 |
| 2008/0288083 A1 * | 11/2008 | Axelsson | A61F 2/30907 623/23.51 |
| 2010/0057216 A1 | 3/2010 | Gannoe et al. | |
| 2010/0070043 A1 | 3/2010 | Kitchen | |
| 2010/0256766 A1 | 10/2010 | Hibri et al. | |

(56) References Cited

U.S. PATENT DOCUMENTS

| | | |
|---|---|---|
| 2011/0035019 A1 | 2/2011 | Goswami et al. |
| 2011/0313532 A1 | 12/2011 | Hunt |
| 2013/0218288 A1* | 8/2013 | Fonte ............... A61L 27/56 623/23.5 |
| 2014/0018814 A1 | 1/2014 | Gillard et al. |
| 2014/0172111 A1 | 6/2014 | Lang et al. |
| 2015/0045903 A1 | 2/2015 | Neal |
| 2016/0015437 A1 | 1/2016 | Elleby et al. |
| 2016/0166284 A1 | 6/2016 | Hacking et al. |
| 2016/0184103 A1 | 6/2016 | Fonte et al. |
| 2016/0262903 A1 | 9/2016 | West |
| 2016/0287388 A1 | 10/2016 | Hunt et al. |
| 2016/0324656 A1* | 11/2016 | Morris ............... A61F 2/30744 |
| 2017/0014235 A1 | 1/2017 | Jones et al. |
| 2017/0020685 A1 | 1/2017 | Geisler et al. |
| 2017/0042697 A1 | 2/2017 | McShane, III et al. |
| 2017/0156766 A1 | 6/2017 | Anderson et al. |
| 2017/0156880 A1 | 6/2017 | Halverson et al. |
| 2017/0216035 A1 | 8/2017 | Hunt |
| 2017/0239064 A1 | 8/2017 | Cordaro |
| 2017/0258606 A1 | 9/2017 | Afzal |
| 2017/0319353 A1 | 11/2017 | Greenhalgh et al. |
| 2018/0064540 A1 | 3/2018 | Hunt et al. |
| 2018/0085230 A1 | 3/2018 | Hunt |
| 2018/0256336 A1 | 9/2018 | Mueller et al. |
| 2018/0256353 A1 | 9/2018 | Nyahay et al. |
| 2018/0296350 A1 | 10/2018 | Hamzey et al. |
| 2018/0338838 A1 | 11/2018 | Cryder et al. |
| 2018/0353268 A1* | 12/2018 | Memmolo ............ A61C 8/0013 |
| 2018/0368981 A1 | 12/2018 | Mattes et al. |
| 2018/0368991 A1 | 12/2018 | Levieux |
| 2019/0038428 A1 | 2/2019 | Stauffer et al. |
| 2019/0060083 A1 | 2/2019 | Weiman et al. |
| 2019/0076266 A1 | 3/2019 | Trudeau et al. |
| 2019/0083282 A1 | 3/2019 | Roeder et al. |
| 2019/0133769 A1 | 5/2019 | Tetsworth et al. |
| 2019/0151113 A1 | 5/2019 | Sack |
| 2019/0159818 A1 | 5/2019 | Schneider et al. |
| 2019/0183653 A1 | 6/2019 | Gregersen et al. |
| 2019/0224023 A1 | 7/2019 | Howard et al. |
| 2019/0254840 A1 | 8/2019 | Gray et al. |
| 2019/0262139 A1 | 8/2019 | Wolters |
| 2019/0274841 A1 | 9/2019 | Hawkes et al. |
| 2019/0298542 A1 | 10/2019 | Kioss |
| 2019/0307574 A1 | 10/2019 | Nyahay et al. |
| 2019/0314169 A1 | 10/2019 | Patel et al. |
| 2019/0328546 A1 | 10/2019 | Palagi et al. |
| 2019/0336305 A1 | 11/2019 | Joly et al. |
| 2019/0343645 A1 | 11/2019 | Miccio et al. |
| 2019/0358058 A1 | 11/2019 | Trieu |
| 2019/0388238 A1 | 12/2019 | Lechmann et al. |
| 2020/0000603 A1 | 1/2020 | McJunkin |
| 2020/0038197 A1 | 2/2020 | Morris et al. |
| 2020/0038198 A1 | 2/2020 | Miccio |
| 2020/0086625 A1 | 3/2020 | O'Neill et al. |
| 2020/0113707 A1 | 4/2020 | Petersheim et al. |
| 2020/0121470 A1 | 4/2020 | Moore et al. |
| 2020/0138595 A1 | 5/2020 | Shoshtaev et al. |
| 2020/0146842 A1 | 5/2020 | Jasinski |
| 2020/0155326 A1 | 5/2020 | Hunt |
| 2020/0179133 A1 | 6/2020 | Ryan |
| 2020/0188120 A1 | 6/2020 | Hamzey et al. |
| 2020/0188129 A1 | 6/2020 | Mcshane, III et al. |
| 2020/0188132 A1 | 6/2020 | Ryan |
| 2020/0188133 A1 | 6/2020 | Mcshane, III et al. |
| 2020/0197189 A1 | 6/2020 | Mazur et al. |
| 2020/0214852 A1 | 7/2020 | Tipping et al. |
| 2020/0222201 A1 | 7/2020 | Mirda et al. |
| 2020/0229940 A1 | 7/2020 | Bishop et al. |
| 2020/0229945 A1 | 7/2020 | Levieux |
| 2020/0237526 A1 | 7/2020 | Wilson et al. |
| 2020/0246160 A1 | 8/2020 | Zappacosta et al. |
| 2020/0261243 A1 | 8/2020 | Unger et al. |
| 2020/0276019 A1 | 9/2020 | Shetty et al. |
| 2020/0281727 A1 | 9/2020 | Dang et al. |
| 2020/0297494 A1 | 9/2020 | Hunt et al. |
| 2020/0297505 A1 | 9/2020 | McLaughlin |
| 2020/0315812 A1 | 10/2020 | Davis et al. |
| 2020/0323645 A1 | 10/2020 | Northcutt et al. |
| 2020/0337851 A1 | 10/2020 | Stampfli et al. |
| 2020/0337855 A1 | 10/2020 | Stauffer et al. |
| 2020/0337856 A1 | 10/2020 | Moore et al. |
| 2020/0345506 A1 | 11/2020 | Ryan et al. |
| 2020/0352735 A1 | 11/2020 | Afzal |
| 2020/0375757 A1 | 12/2020 | Sack |
| 2020/0375758 A1 | 12/2020 | Northcutt et al. |
| 2020/0376174 A1 | 12/2020 | Melkent et al. |

FOREIGN PATENT DOCUMENTS

| | | |
|---|---|---|
| EP | 0016480 A1 | 2/1980 |
| JP | 2007151805 | 6/2007 |
| WO | 2005051233 A1 | 6/2005 |
| WO | 2013091085 A1 | 6/2013 |
| WO | 2013181375 A1 | 12/2013 |

OTHER PUBLICATIONS

European Search Report dated Jul. 31, 2020 from EP Application No. 17863416.8.

L.E. Murr et al., "Next-generation biomedical implants using additive manufacturing of complex, cellular and functional mesh arrays", Philosophical Transactions of the Royal Society, vol. 368, Mar. 22, 2010, pp. 1999-2032, XP055149555, ISSN: 1878-5905, DOI: 10.1098/rsta.2010.0010 (pp. 25-29; Fig. 2B).

Office Action dated Mar. 25, 2021 for CN Application No. 2019-543184.

* cited by examiner

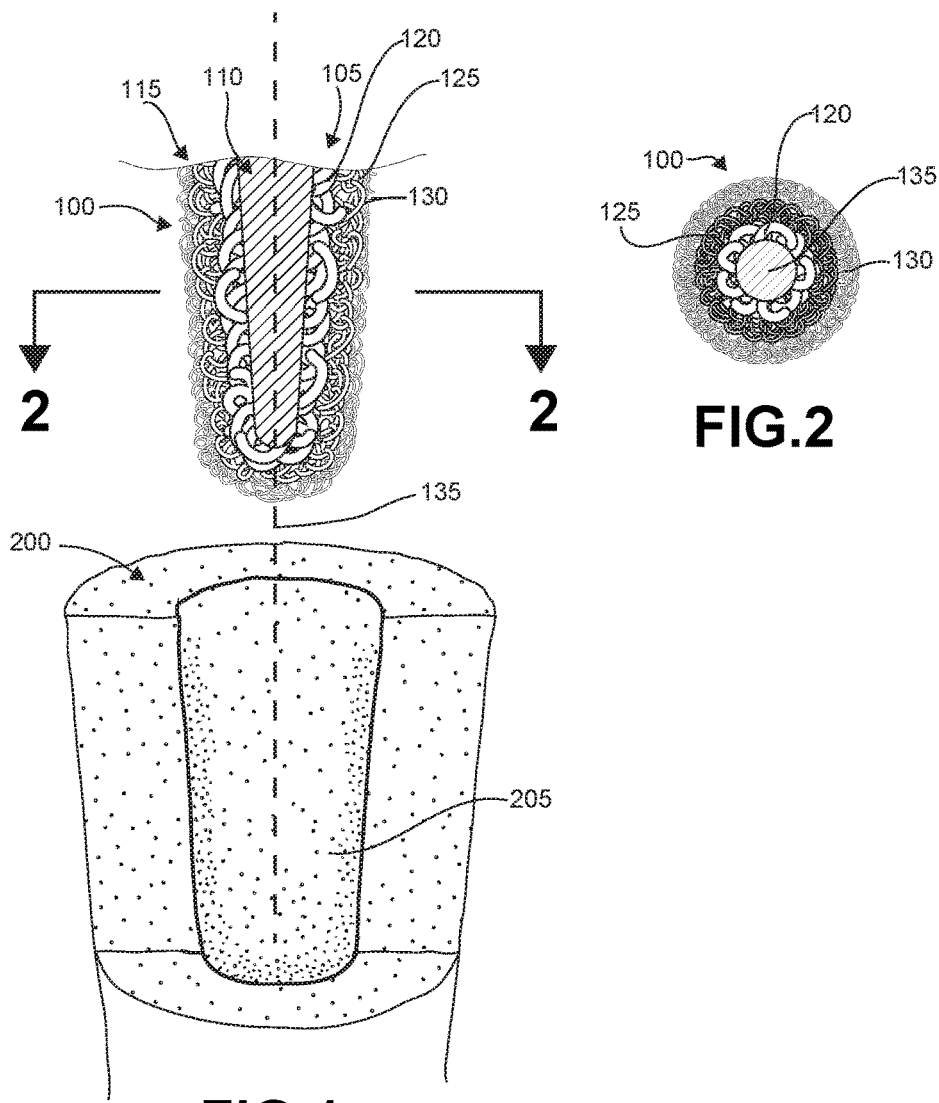
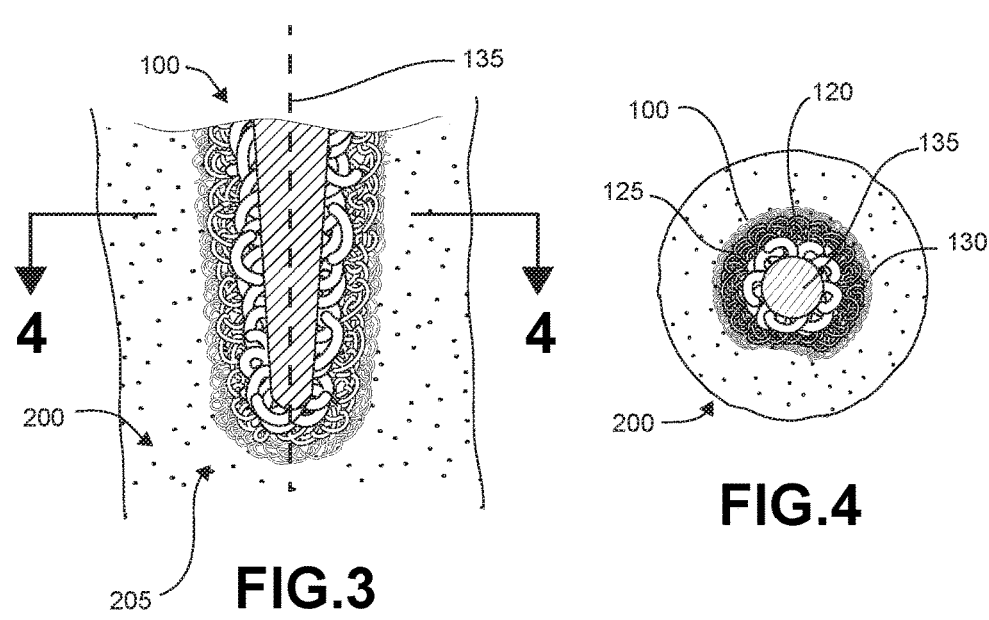

IMPLANT WITH MULTI-LAYER BONE INTERFACING LATTICE

RELATED APPLICATIONS

This application claims priority to U.S. Provisional Application No. 62/412,657, filed Oct. 25, 2016, which is incorporated herein by reference.

BACKGROUND

The embodiments are generally directed to implants for supporting bone growth in a patient.

A variety of different implants are used in the body. Implants used in the body to stabilize an area and promote bone ingrowth provide both stability (i.e. minimal deformation under pressure over time) and space for bone ingrowth.

Some implants include portions that are inserted within recesses in bone. In some cases, at least a portion of an implant receiving recess may be generally preformed in the bone. For example, at least a portion of an implant receiving recess may be formed by a medullary cavity. In such cases, tools may be used to drill or ream out the cavity further. In other cases, the recess is completely formed in the bone with tools. The portions of implants that are inserted within recesses in bone often include structural features that facilitate bone ingrowth and securing the implant within the bone. For example, some implants include texture on the bone contacting surface. Some implants include porous surfaces, or gaps between structural members that permit bone ingrowth.

In some cases the inner surfaces of the recess within the bone may have irregularities due to the natural shape of the bone and/or imperfections in the surfaces prepared by the tools. Such irregularities can reduce the amount of surface contact between the bone and the implant, which can limit the effectiveness of the mechanical fixation of the implant within the bone.

SUMMARY

The present disclosure is directed to implants having a substrate and a multi-layer bone interfacing lattice, wherein the layers have varying compressibility to conform to the irregularities in the recess within the bone. For example, the layers may be formed by a lattice of elongate curved structural members. Layers closest to the substrate may have less compressibility, and layers further away from the substrate may have more compressibility.

In one aspect, an implant may include a body including a substrate and a bone interfacing lattice disposed on the substrate. The bone interfacing lattice includes at least two layers of elongate curved structural members. In addition, the at least two layers of elongate curved structural members include a first layer adjacent the substrate and a second layer adjacent the first layer. Also, the first layer has a first deformability and the second layer has a second deformability, wherein the second deformability is greater than the first deformability.

In another aspect, an implant includes a body including a substrate and a bone interfacing lattice disposed on the substrate. The bone interfacing lattice includes at least two layers of elongate curved structural members. In addition, the at least two layers of elongate curved structural members includes a first layer adjacent the substrate and a second layer adjacent the first layer. Also, the first layer has a first compressibility and the second layer has a second compressibility, wherein the second compressibility is less than the first compressibility.

In another aspect, an implant includes a body including a substrate and a bone interfacing lattice disposed on the substrate. The bone interfacing lattice includes at least two layers of elongate curved structural members. In addition, the at least two layers of elongate curved structural members includes a first layer adjacent the substrate and a second layer adjacent the first layer. Also, the elongate curved structural members of the first layer have a first gauge and the elongate curved structural members of the second layer have a second gauge, wherein the second gauge is less than the first gauge.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

FIG. 1 is a schematic cutaway cross-sectional view of a bone having a recess and a longitudinal cross-sectional view of a portion of an implant configured to be inserted into the recess in the bone;

FIG. 2 is a schematic transverse cross-sectional view of the implant shown in FIG. 1;

FIG. 3 is a schematic cross-sectional view of the bone of FIG. 1 with the implant inserted into the recess;

FIG. 4 is a schematic transverse cross-sectional view of the bone and implant inserted as shown in FIG. 3;

DETAILED DESCRIPTION

Figure 5:
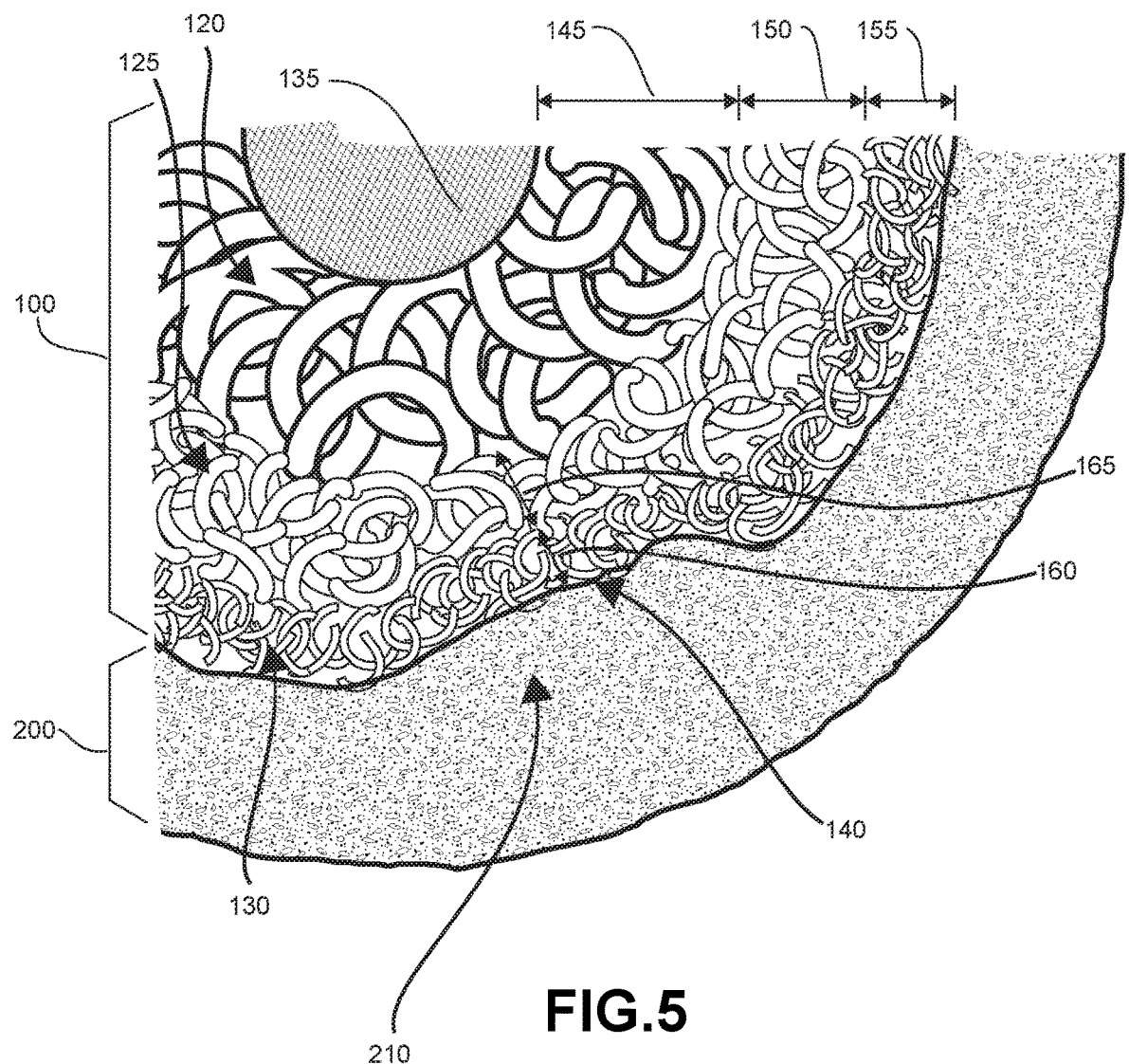
FIG. 5 is a schematic enlarged version of the cross-sectional view of the bone and implant shown in FIG. 4.

The embodiments described herein are directed to implants including portions for insertion within recesses in bone. The portions configured for insertion within the recesses each include a body having a substrate or central portion and a multi-layer bone interfacing lattice. The layers of the bone interfacing lattice may include elongate curved structural members. Such structural members may have any of a variety of curved configurations. For example, the structural members may include portions that are helical, spiraled, coiled, sinusoidal, arched, or otherwise curved. Examples of such curved configurations are provided in the following applications.

In addition to the various provisions discussed below, any of the embodiments disclosed herein may make use of any of the body/support structures, frames, plates, coils or other structures disclosed in McShane III et al., U.S. Pat. No. 10,478,312, issued on Nov. 19, 2019, and titled "Implant with Protected Fusion Zones," and which is incorporated herein by reference in its entirety. For purposes of convenience, this application will be referred to throughout the present application as "The Protective Fusion Zones application."

Also, any of the embodiments disclosed herein may make use of any of the body/support structures, elements, frames, plates or other structures disclosed in McShane III et al., U.S. Publication Number 2017/0042697, published on Feb. 16, 2017, and titled "Implant with Arched Bone Contacting Elements," and which is incorporated herein by reference in its entirety.

Also, any of the embodiments disclosed herein may make use of any of the body/support structures, elements, frames, plates or other structures disclosed in Bishop et al., U.S. Pat. No. 10,512,549, issued on Dec. 24, 2019, and titled "Implant with Structural Members Arranged Around a Ring," and which is incorporated herein by reference in its entirety and referred to herein as "The Ring application."

Also, any of the embodiments disclosed herein may make use of any of the body/support structures, elements, frames, plates, or other structures disclosed in Morris et al., U.S. Publication Number 2016/0324656, published on Nov. 10, 2016, and titled "Coiled Implants and Systems and Methods of Use Thereof," and which is incorporated herein by reference in its entirety and referred to herein as "The Coiled Implant Application."

Also, any of the embodiments disclosed herein may make use of any of the body/support structures, elements, frames, plates, or other structures disclosed in Nyahay et al., U.S. Pat. No. 10,357,377, issued on Jul. 23, 2019, and entitled "Implant with Bone Contacting Elements Having Helical and Undulating Planar Geometries," and which is incorporated herein by reference in its entirety.

Also, any of the embodiments disclosed herein may make use of any of the body/support structures, elements, frames, plates, or other structures disclosed in Nyahay et al., U.S. Pat. No. 10,667,924, issued on Jun. 2, 2020, and entitled "Corpectomy Implant," and which is incorporated herein by reference in its entirety.

Also, any of the embodiments disclosed herein may make use of any of the body/support structures, elements, frames, plates, or other structures disclosed in Bishop et al., U.S. Pat. No. 10,213,317, issued on Feb. 26, 2019, and entitled "Implant with Supported Helical Members," and which is incorporated herein by reference in its entirety.

As used herein, the term "fixedly attached" shall refer to two components joined in a manner such that the components may not be readily separated (for example, without destroying one or both components).

For purposes of clarity, reference is made to various directional adjectives throughout the detailed description and in the claims. As used herein, the term "anterior" refers to a side or portion of an implant that is intended to be oriented towards the front of the human body when the implant has been placed in the body. Likewise, the term "posterior" refers to a side or portion of an implant that is intended to be oriented towards the back of the human body following implantation. In addition, the term "superior" refers to a side or portion of an implant that is intended to be oriented towards a top (e.g., the head) of the body while "inferior" refers to a side or portion of an implant that is intended to be oriented towards a bottom of the body. Reference is also made herein to "lateral" sides or portions of an implant, which are sides, or portions, facing along a lateral direction of the body (and which correspond with the left or right sides of a patient).

An implant may also be associated with various reference planes or surfaces. As used herein, the term "median plane" refers to a vertical plane which passes from the anterior side to the posterior side of the implant, dividing the implant into right and left halves, or lateral halves. As used herein, the term "transverse plane" refers to a horizontal plane that divides the implant into superior and inferior portions. As used herein, the term "coronal plane" refers to a vertical plane located in the center of the implant that divides the implant into anterior and posterior halves. In some embodiments, the implant is symmetric about one or more of these planes.

FIG. 1 is a schematic cutaway cross-sectional view of a bone having a recess and a longitudinal cross-sectional view of a portion of an implant configured to be inserted into the recess in the bone. As shown in FIG. 1, a portion of an implant 100 may include a body 105. Body 105 may include a substrate 110 and a bone interfacing lattice 115 disposed on substrate 110.

Bone interfacing lattice 115 may be fixedly attached to substrate 110 in any suitable manner. For example, in some embodiments, body 105 may be 3D printed, such that substrate 110 and bone interfacing lattice 115 are a continuous unitary structure. In other embodiments, bone interfacing lattice 115 may be sintered, welded, thermally bonded, or otherwise joined to substrate 115.

FIG. 1 also shows a portion of a bone 200, illustrated in a cutaway cross-sectional view. As shown in FIG. 1, bone 200 includes a recess 205. In some cases, recess 205 may be substantially naturally occurring in the bone. For example, in some cases, recess 205 may be a medullary cavity. In order prepare a medullary cavity for insertion of an implant, bone marrow may be removed from the medullary cavity. In addition, portions of the cancellous bone lining the medullary cavity may also be removed, to provide an inner bone surface that is primarily cortical bone. In other cases, recess 205 may be wholly formed by surgical tools. For example, in some cases, a recess may be bored, reamed, or otherwise surgically formed in cortical bone or trabecular bone.

Portions of implants configured to be inserted into recesses in bone may include provisions to promote bone ingrowth. For example, bone interfacing surfaces of implants may include porous structures, such as a lattice of elongate curved structural members. In some embodiments, the porous structures may include provisions to maximize the amount of surface contact between the porous bone interfacing lattice of the implants and the bone. For example, in some embodiments, the bone interfacing lattice may include portions that are conformable to the interior wall of the recess in the bone.

As shown in FIG. 1, in some embodiments, body 105 of implant 100 may have a substantially elongate shape configured to be inserted into recess 205 in bone 200. For example, body 105 may be elongate along a central longitudinal axis 135. Body 105 of implant 100 is illustrated as being a substantially conical shape. Other elongate shapes are also envisioned, including substantially cylindrical rods or posts. Further, any suitable cross-sectional shape may be used, including circular, oval, square, rectangular, triangular, and any other suitable shape.

The bone interfacing lattice may include at least two layers having differing deformabilities. For example, inner layers (positioned closer to the substrate) may have a low deformability (or even substantially no deformability in practical use). Outer layers (positioned further from the substrate) may have greater deformability. Accordingly, these outer layers may deform in order to conform to the inner wall of the recess in the bone. The bone interfacing lattice includes at least two layers of elongate curved structural members. In some embodiments, the bone interfacing lattice may have three or more layers of elongate curved structural members, wherein the three or more layers have differing deformabilities.

As shown in FIG. 1, bone interfacing lattice 115 may include three layers. For example, a first layer 120 may be disposed adjacent substrate 110. In addition, lattice 115 may include a second layer 125 disposed adjacent first layer 120 outward of first layer 120 relative to central longitudinal axis 135. Also, lattice 115 may include a third layer 130 adjacent second layer 125 and outward of second layer 125.

The layers of bone interfacing lattice 115 may be fixedly attached to one another in any suitable manner. For example, in some embodiments, body 105 may be 3D printed, such that the layers form a continuous unitary structure. In other embodiments, the layers may be sintered, welded, thermally bonded, or otherwise joined to one another. In addition, first layer 120 may be fixedly attached to substrate 110.

First layer 120 may have a first deformability, second layer 125 may have a second deformability, and third layer 130 may have a third deformability. In some embodiments, the second deformability of second layer 125 may be greater than the first deformability of first layer 120. In addition, the third deformability of third layer 130 may be greater than the second deformability of second layer 125.

Each layer of the lattice structure may include a plurality of elongate curved structural members. The configuration of the elongate curved structural members may vary from layer to layer in order to provide the respective layers with differing amounts of deformability. The layers can be deformable in any of a variety of ways (e.g., elastic vs. plastic deformation) described in more detail below. In addition, the configuration of the elongate curved structural members can differ in a variety of ways to provide the variance in deformability.

In some embodiments, the respective layers may be provided with differing amounts of elastic deformability. In some embodiments, the respective layers may be provided with differing amounts of plastic deformability. In some embodiments, a given layer may be configured to maintain its thickness but deform by bending as a whole. In other cases, a layer may be configured to collapse, for example, by compressing. Thus, in some embodiments, the layers of the lattice may have different compressibilities. For example, in some embodiments, outer layers may be more compressible than inner layers. That is, the outer layers may have a greater capacity for the thickness of the layers to collapse. In some embodiments, the further the layer is from the substrate of the implant, the greater the compressibility, with the outermost (i.e., bone contacting) layer being the most compressible.

In some embodiments, a combination of varying compressibility and varying deformability may be utilized. For example, in some embodiments, an innermost layer may be substantially non-deformable, an outermost layer may be deformable by bending, but may maintain its thickness despite deforming. That is, the outermost layer may deflect inward in order to conform to the inner surface of the bone recess. In order to permit the inward deflection of the outermost layer, an intermediate layer between the innermost layer and the outermost layer may be relatively compressible. Thus, the compressible intermediate layer may collapse in various locations to accommodate the inward deflection of the outermost layer. However, since the outermost layer does not collapse to reduce its thickness, the porosity of the outermost layer may be preserved in deflected areas, which may maximize the capacity of the outermost bone contacting layer to permit bone ingrowth. Other arrangements of layers having differing deformabilities are also possible. Among other alternatives, more than three layers may be used to form the lattice. In some embodiments, different portions of the same lattice layer may have different deformabilities.

In some embodiments, the densities of the elongate curved structural members may vary. For example, outer layers may have lower densities than inner layers. For purposes of this disclosure, the term densities shall refer to ratio of open space to volume occupied by elongate curved structural members. A lower density of structural members provides a layer with greater porosity. Thus, lower densities in the outer layers provide a more porous bone contacting surface. The greater porosity may facilitate bone ingrowth. In addition, the greater porosity may enable the outer layers to maintain a desired level of porosity even when the layers are partially compressed upon implantation.

In some embodiments, the outer layers may be formed of different materials than the inner layers. For example, in some embodiments, the outer layers may be formed of more flexible or more deformable materials than the inner layers.

In some embodiments, the gauge of the elongate curved structural members may differ from layer to layer. That is, the cross-sectional size of the elongate curved structural members may be larger in some layers and smaller in other layers. For example, in some embodiments, the further from the substrate a layer is disposed, the smaller the gauge of the elongate curved structural members in the layer. The smaller gauge renders the structural members to be more deformable (plastically or elastically).

As shown in FIG. 1, each of first layer 120, second layer 125, and third layer 130 are formed of elongate curved structural members. Such structural members may have any of a variety of curved configurations. For example, the structural members may include portions that are helical, spiraled, coiled, sinusoidal, arched, or otherwise curved.

The configuration of curved structural members may be regular or irregular. That is, the members may be arranged in a regular pattern or in a random arrangement. Some of the structural members within each layer may overlap or intersect with one another. In some cases, the cross-sectional size and/or shape of a structural member could vary along its length (e.g., the diameter could change along the length of a structural member).

Embodiments can include provisions for protecting bone growth along and adjacent to elongate curved structural members of an implant. In some embodiments, an elongate curved structural member can be configured with a geometry that helps to protect new bone growth in selected regions or "protected fusion zones." In some embodiments, an elongate curved structural member can have a spiral, helical or twisted geometry that provides a series of such protected fusion zones for enhanced bone growth.

Some elongate curved structural members may have a generalized helical geometry. As used herein, a "generalized helical geometry" or "spiraling geometry" refers to a geometry where a part (portion, member, etc.) winds, turns, twists, rotates or is otherwise curved around a fixed path. In some cases, the fixed path could be straight. In other cases, the fixed path can be curved. In the present embodiments, for example, the fixed path is generally a combination of straight segments and curved segments.

Curves having a generalized helical geometry (also referred to as generalized helical curves) may be characterized by "coils," "turns," or "windings" about a fixed path. Exemplary parameters that may characterize the specific geometry of a generalized helical curve can include coil diameter (including both a major and minor diameter) and the pitch (i.e., spacing between adjacent coils). In some cases, the "amplitude" of a coil or loop may also be used to describe the diameter or widthwise dimension of the coil or loop. Each of these parameters could be constant or could vary over the length of a generalized helical curve.

Generalized helical curves need not be circular or even round. In some embodiments, for example, a generalized helical curve could have linearly-segmented shape (or locally polygonal shape) such that each "coil" or "turn" is comprised of straight line segments rather than arcs or other curved segments. Generalized helical curves may also include combinations of curved and straight segments.

The arrangement of elongate curved structural members may be designed to achieve a desired total open volume. As used herein a total open volume is the combined volume of any openings between structural members or between structural members and the substrate. This open configuration may facilitate bone growth in and through the implant. A portion, or substantially all of, the open spaces may be filled with a bone graft or bone growth promoting material prior to insertion of the implant to facilitate bone growth.

The implantation process may begin with the application of a bone growth promoting material, also referred to as a BGPM, to the implant. As used herein, a "bone growth promoting material" is any material that helps bone growth. Bone growth promoting materials may include provisions that are freeze dried onto a surface or adhered to the metal through the use of linker molecules or a binder. Examples of bone growth promoting materials are any materials including bone morphogenetic proteins (BMPs), such as BMP-1, BMP-2, BMP-4, BMP-6, and BMP-7. These are hormones that convert stem cells into bone forming cells. Further examples include recombinant human BMPs (rhBMPs), such as rhBMP-2, rhBMP-4, and rhBMP-7. Still further examples include platelet derived growth factor (PDGF), fibroblast growth factor (FGF), collagen, BMP mimetic peptides, as well as RGD peptides. Generally, combinations of these chemicals may also be used. These chemicals can be applied using a sponge, matrix or gel.

Some bone growth promoting materials may also be applied to an implantable prosthesis through the use of a plasma spray or electrochemical techniques. Examples of these materials include, but are not limited to, hydroxyapatite, beta tri-calcium phosphate, calcium sulfate, calcium carbonate, as well as other chemicals.

A bone growth promoting material can include, or may be used in combination with a bone graft or a bone graft substitute. A variety of materials may serve as bone grafts or bone graft substitutes, including autografts (harvested from the iliac crest of the patient's body), allografts, demineralized bone matrix, and various synthetic materials.

Some embodiments may use autograft. Autograft provides the implantation site with calcium collagen scaffolding for the new bone to grow on (osteoconduction). Additionally, autograft contains bone-growing cells, mesenchymal stem cells and osteoblast that regenerate bone. Lastly, autograft contains bone-growing proteins, including bone morphogenic proteins (BMPs), to foster new bone growth in the patient.

Bone graft substitutes may comprise synthetic materials including calcium phosphates or hydroxyapatites, stem cell containing products which combine stem cells with one of the other classes of bone graft substitutes, and growth factor containing matrices such as INFUSE® (rhBMP-2-containing bone graft) from Medtronic, Inc.

It should be understood that the provisions listed here are not meant to be an exhaustive list of possible bone growth promoting materials, bone grafts, or bone graft substitutes.

In some embodiments, BGPM may be applied to one or more outer surfaces of an implant. In other embodiments, BGPM may be applied to internal volumes within an implant. In still other embodiments, BGPM may be applied to both external surfaces and internally within an implant.

As shown in FIG. 1, the elongate curved structural members of first layer 120 may have a first gauge, the elongate curved structural members of second layer 125 may have a second gauge, and the elongate curved structural members of third layer 130 may have a third gauge. As further shown in FIG. 1, the second gauge may be smaller than the first gauge, and the third gauge may be smaller than the second gauge. This difference in gauges may provide each of the layers with a different deformability.

Accordingly, the dimensions of the elongate curved structural members can vary. In some embodiments, the elongate curved structural members can have cross-sectional diameters ranging between 0.2 and 3 mm. For example, in some embodiments the elongate curved structural members of first layer 120 may be approximately 1.0 mm in diameter, the elongate curved structural members of second layer 125 may be approximately 0.6 mm in diameter, and the elongate curved structural members of third layer 130 may be approximately 0.3 mm in diameter.

FIG. 2 is a schematic transverse cross-sectional view of the implant shown in FIG. 1. As shown in FIG. 2, first layer 120 may have a first thickness that is substantially consistent such that an outer shape of first layer 120 is substantially the same as the outer shape of substrate 110. In addition, second layer 125 may have a second thickness that is substantially consistent such that the outer shape of second layer 125 is substantially the same as the outer shape of first layer 120. Further, third layer 130 may have a third thickness that is substantially consistent such that the outer shape of third layer 130 is substantially the same as the outer shape of second layer 125. In other words, in some embodiments, the interfaces between layers may be concentric.

In some embodiments, the interface between layers may have a substantially negligible thickness. In other embodiments, the interface between the first layer and the second layer is a transition region having a thickness within which the elongate curved structural members of the first layer are intermingled with the elongate curved structural members of the second layer. Similarly, the interface between the second layer and the third layer may also be a transition region having a thickness, within which the elongate curved structural members of the second layer are intermingled with the elongate curved structural members of the third layer.

Implant 100 may be configured to be implanted within any of a variety of bones within the body of a human or animal. In some embodiments, body 105 of implant 100 may be configured for implantation into the medullary cavity of long bones, such as the femur or humerus. In some embodiments, body 105 of implant 100 may be configured for implantation into a drilled or reamed recess in cortical or trabecular bone.

FIG. 3 is a schematic cross-sectional view of bone 200 of FIG. 1 with body 105 of implant 100 inserted into recess 205. In addition, FIG. 4 is a schematic transverse cross-sectional view of bone 200 and implant 100 inserted as shown in FIG. 3. As shown in FIGS. 3 and 4, portions of third layer 130 and portions of second layer 125 may be deformed to conform with irregularities in the inner surface of recess 205. In an area where bone 200 protrudes into recess 205, such as protrusion 210 in FIG. 4, one or more layers of implant 100 may deform as shown by a deformed area 140 in FIG. 4.

FIG. 5 is a schematic enlarged cross-sectional view of bone 200 and implant 100. FIG. 5 generally illustrates the different gauges of the elongate structural members in first layer 120, second layer 125, and third layer 130. It will be noted that depiction of the size, shape, and general configuration of these layers is intended to be schematic. The elongate curved structural members can have any suitable shape and arrangement. The present disclosure is directed to the properties of the multi-layer lattice in terms of the relative deformabilities of the layers.

As shown in FIG. 5, one or more layers of the lattice of implant 100 are deformable. Protrusion 210 of bone 200 represents an irregularity in a bone recess. While surgical tools are generally able to prepare a bone recess with minimal irregularities, the relative size of protrusion 210 is exaggerated in FIG. 5 for purposes of illustration. As shown in FIG. 5, two of the layers of the lattice are deformed by protrusion 210, resulting in a reduction in the thickness of the two deformed layers at the location of protrusion 210. In particular, first layer 120 has a first undeformed thickness of 145, second layer 125 has a second undeformed thickness 150, and third layer 130 has a third undeformed thickness 155. In the deformed area, third layer 130 has a deformed thickness 160 that is smaller than third undeformed thickness 155. In addition, second layer 125 has a deformed thickness 165 that is smaller than second undeformed thickness 150. In some embodiments, the deformability of the layers may differ. For example, in some embodiments, third layer 130 may deform more than second layer 125.

Figure 6:
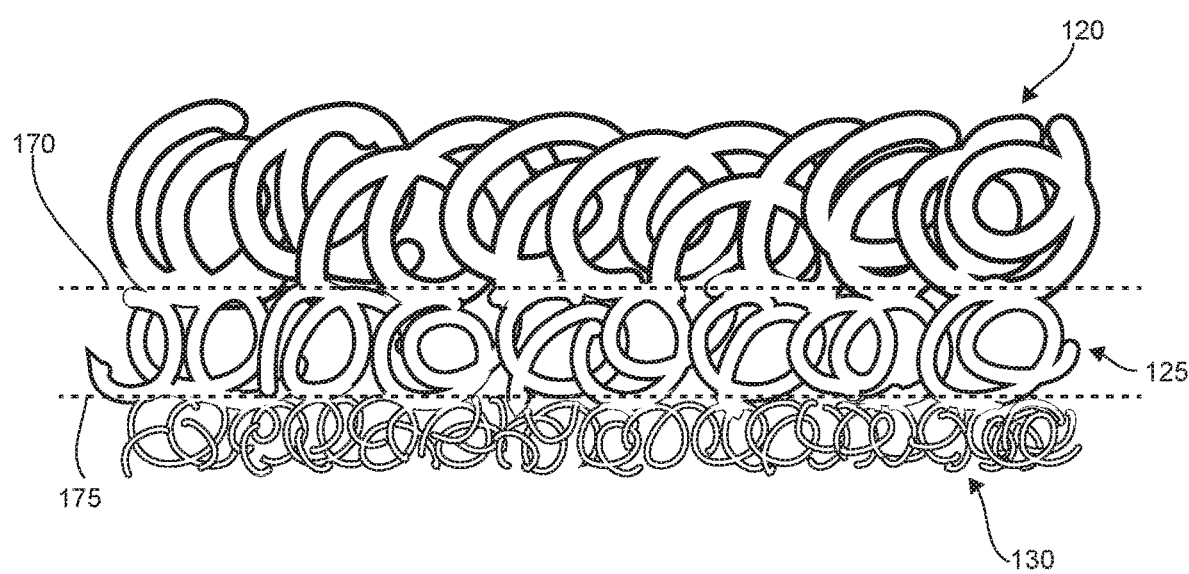
FIG. 6 is a schematic enlarged view of three layers of elongate curved structural members.

FIG. 6 is a schematic enlarged view of three layers of elongate curved structural members. In some embodiments, the layers may be formed as a single unitary structure, for example, by 3D printing. As shown in FIG. 6, in some embodiments, the transition between one layer to the next layer may occur in two dimensions. That is, the transition may have no thickness, such that adjacent layers are completely discreet. For example, as shown in FIG. 6, a first transition 170 between first layer 120 and second layer 125 may have no thickness. Similarly, a second transition 170 between second layer 125 and third layer 130 may also have no thickness. This configuration may ensure that the deformabilities of the respective layers remain unchanged by the transitions between layers.

Figure 7:
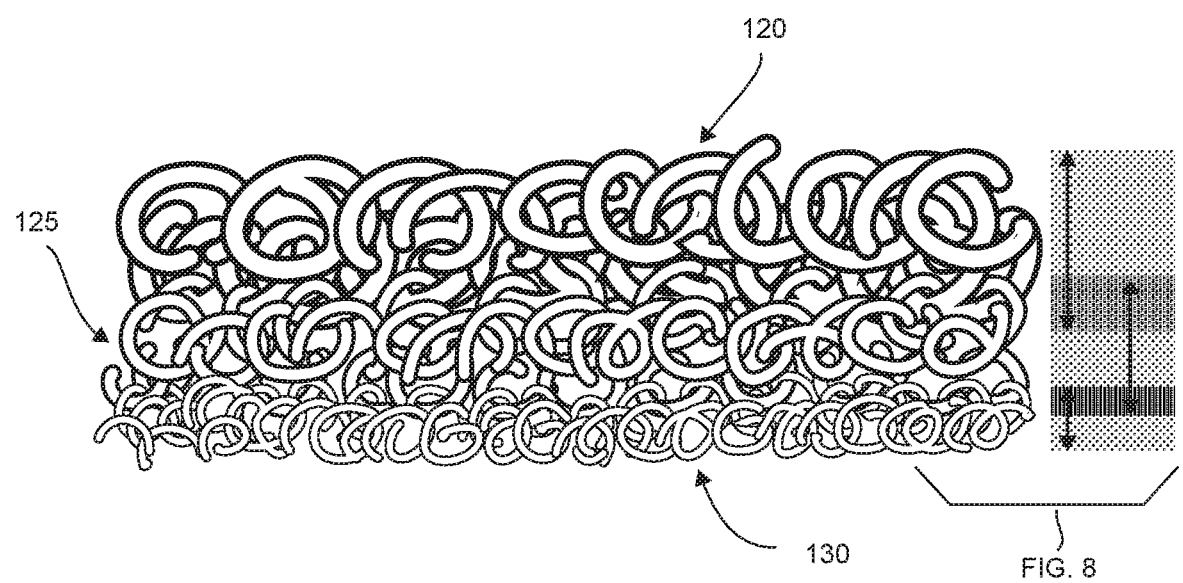
FIG. 7 is a schematic enlarged view of three layers of elongate curved structural members wherein the layers intermingle with one another at the respective boundaries.
Figure 8:
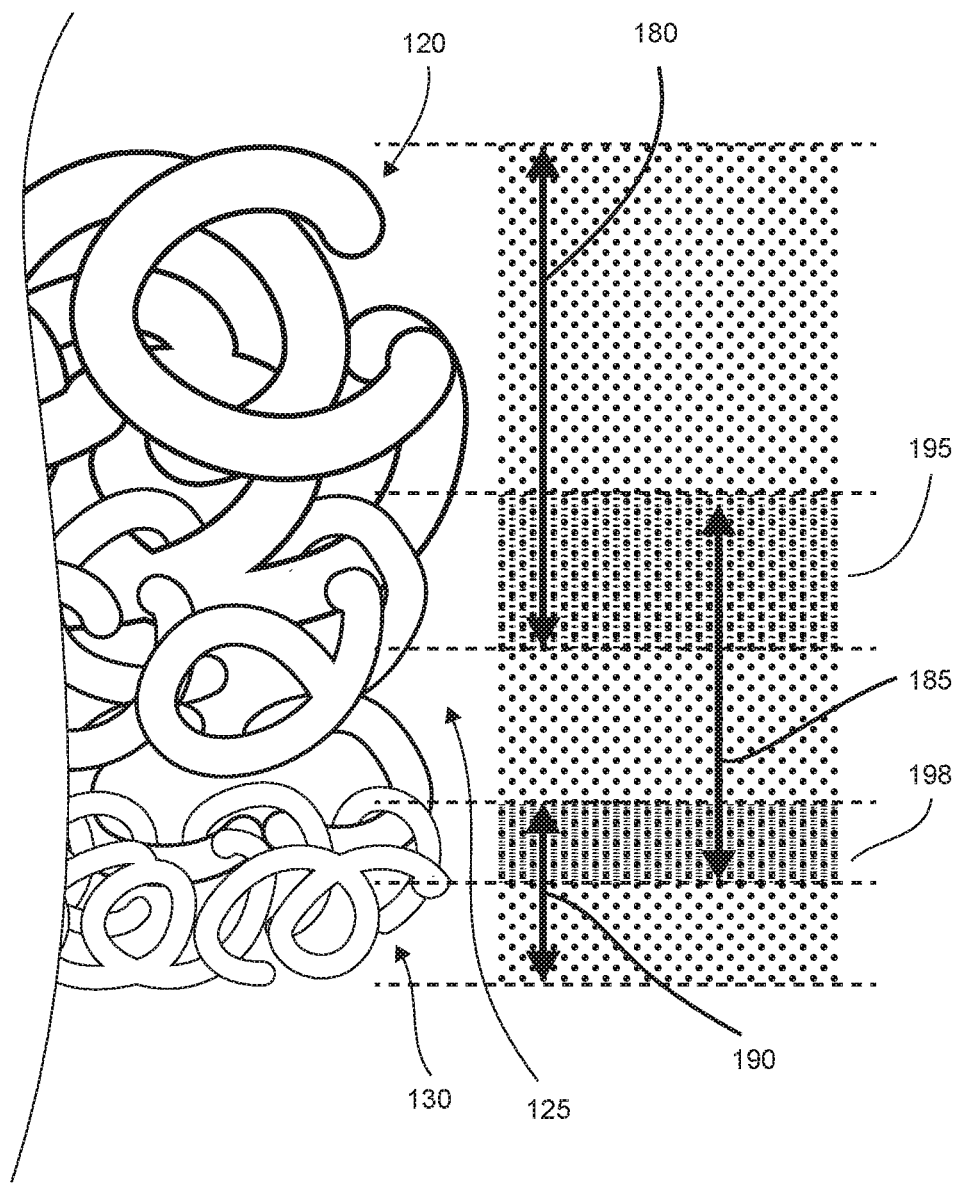
FIG. 8 is a schematic further enlarged view of the three layers of elongate curved structural members shown in FIG. 7.

FIG. 7 is a schematic enlarged view of three layers of elongate curved structural members wherein the layers intermingle with one another at the respective boundaries. FIG. 8 is a schematic further enlarged view of the three layers of elongate curved structural members shown in FIG. 7. As shown in FIG. 8, in some embodiments, the transitions between layers may have a thickness. That is, there is a portion of the lattice where elongate curved structural members from one layer intermingle with the elongate curved structural members of the adjacent layer. FIG. 8 illustrates first layer 120 as having a first thickness 180, second layer 125 as having a second thickness 185, and third layer 130 as having a third thickness 190. As further shown in FIG. 8, first layer 120 and second layer 125 may intermingle to form a transition region 195, which has a thickness, and therefore a volume. Similarly, second layer 125 may intermingle with third layer 130 to form a second transition region 198, which has a thickness, and therefore a volume. This configuration may provide the lattice with additional strength, and prevent delamination of layers.

In some embodiments, some layer transitions may have a thickness, and others may not. For example, in some embodiments, the transition between the first (innermost) layer and the second layer may have a thickness, whereas the transition between the second (middle) layer and the third (outermost) layer may not have a thickness. In such embodiments, since the first layer may not deform much, if at all, having a transition with thickness to the second layer may not unduly alter the deformability of the first layer. Whereas, for the transition between the second layer and the third layer, a transition without thickness may be preferred in order to maintain the relative deformability properties of the respective layers and the lattice as a whole.

FIGS. 3-5 are schematic illustrations intended to generally illustrate a portion of an implant having a multi-layer bone interfacing lattice inserted into a portion of a bone. FIGS. 3-5 are not intended to be specific to a particular type of implant or a particular type of bone. FIGS. 9-16 illustrate exemplary embodiments in which such a multi-layer bone interfacing lattice may be implemented.

Figure 9:
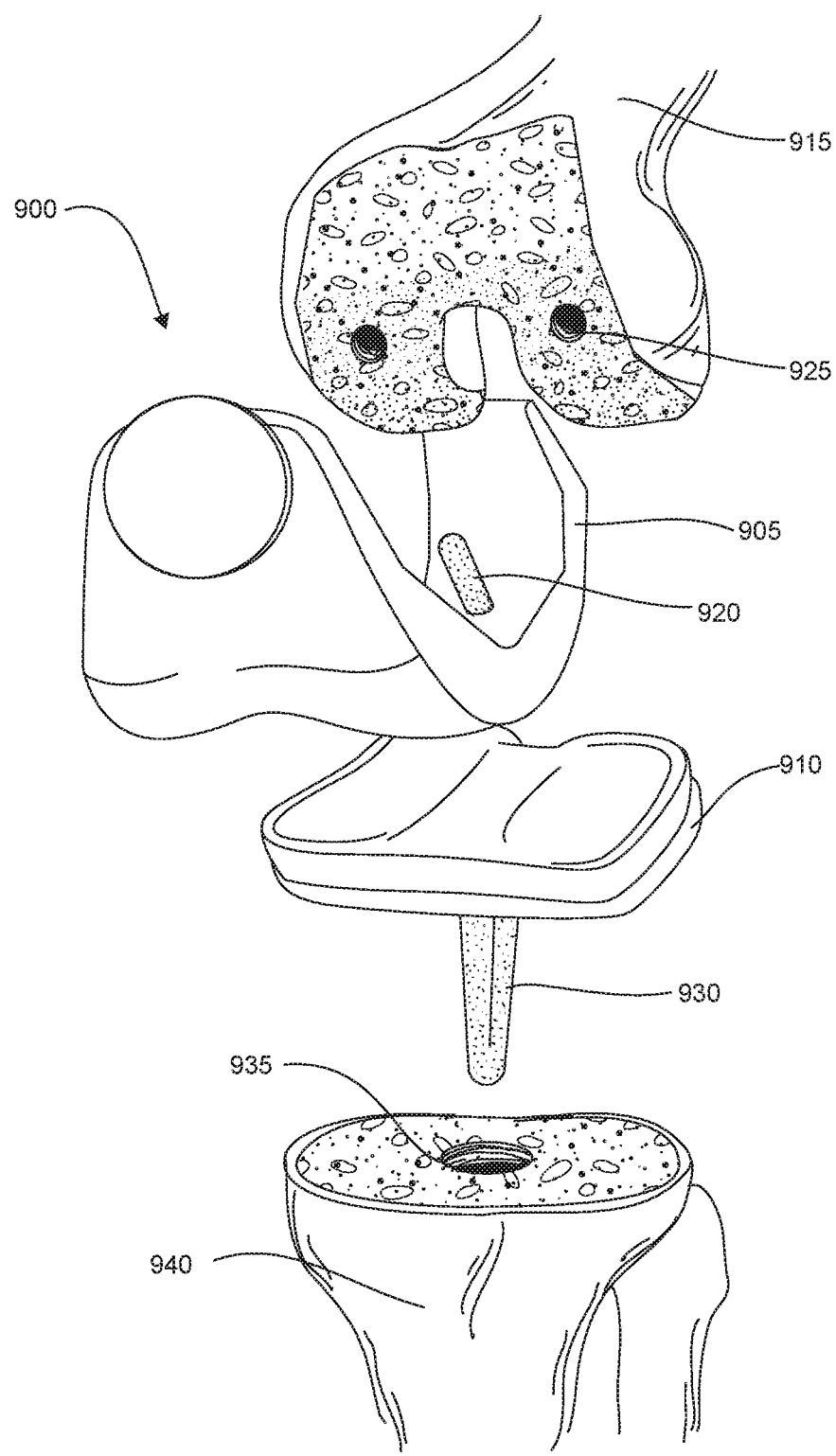
FIG. 9 is a schematic exploded view of a knee replacement implant system according to an exemplary embodiment.

FIG. 9 is a schematic exploded view of a knee replacement implant system according to an exemplary embodiment. There are multiple components of a knee replacement system that can implement a multi-layer bone interfacing lattice. As shown in FIG. 9, a knee replacement implant system 900 may include a femoral component 905 and a tibial component 910. Femoral component 905 may be configured for mounting onto the distal end of a femur 915. Femoral component 905 may include one or more posts 920 configured to be inserted into holes 925 in femur 915 which are drilled by the surgeon. Posts 920 may include a multi-layer bone interfacing lattice to facilitate maximum bone contacting surface within holes 925. Stippling indicates general areas of posts 920 that may include a multi-layer bone interfacing lattice. Tibial component 910 may also include a post 930 configured for insertion into a recess 935 in the proximal end of a tibia 940. Recess 935 may include a portion of the medullary cavity within the tibia, and may also be at least partially formed by the surgeon via cutting, drilling, reaming, or other bone shaping processes. Post 930 may also include a multi-layer bone interfacing lattice to facilitate maximum bone contacting surface within recess 935. Stippling indicates general areas of post 930 that may include a multi-layer bone interfacing lattice.

In some embodiments, a multi-layer bone interfacing lattice may be implemented on metaphyseal sleeves. Such sleeves are utilized, for example, during revision surgeries when a significant amount of bone resorption has taken place. The sleeves take up the space between an implant post and the inner surface of the bone recess, which has become enlarged due to bone resorption and/or further reaming performed to prepare the recess for a new implant.

Figure 10:
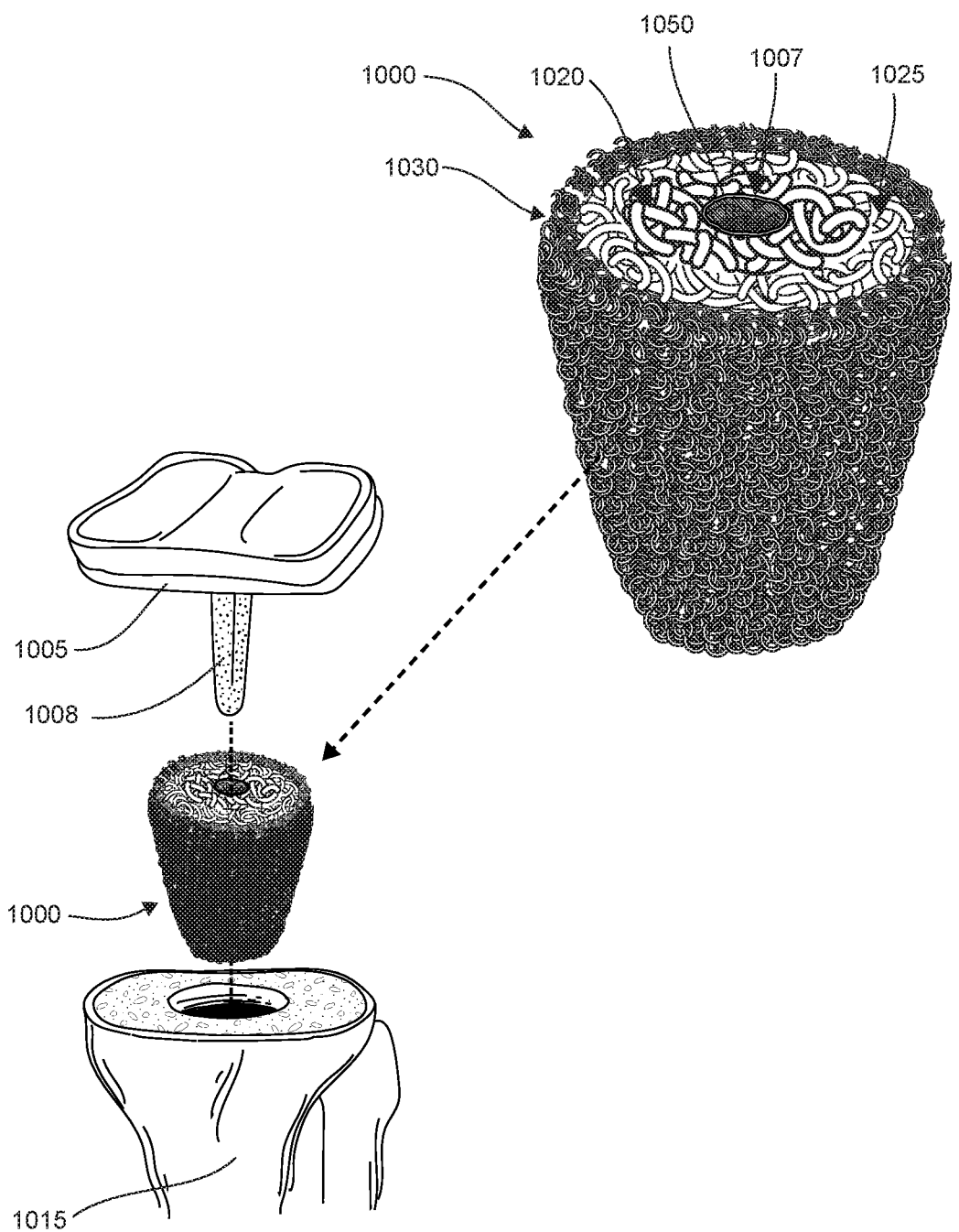
FIG. 10 is a schematic exploded view of a portion of a knee replacement system including a metaphyseal sleeve.

FIG. 10 is a schematic exploded view of a metaphyseal sleeve 1000 and a tibial plateau implant 1005. As illustrated in FIG. 10, metaphyseal sleeve 1000 may include a central hole 1007 configured to receive a post 1008 of tibial plateau implant 1005. In addition, sleeve 1000 may include a bone interfacing lattice configured for implantation in a proximal end of a tibia 1015. The lattice may include a plurality of concentric layers formed of elongate curved structural members. As shown in FIG. 10, the lattice may include a first layer 1020, a second layer 1025, and a third layer 1030.

As further shown in FIG. 10, first layer 1020 may include elongate curved structural members having a first gauge. Second layer 1025 may include elongate curved structural members having a second gauge. Third layer 1030 may include elongate curved structural members having a third gauge. As shown in FIG. 10, the second gauge may be smaller than the first gauge, and the third gauge may be smaller than the second gauge.

As also shown in FIG. 10, in some embodiments, implant 1000 may include an inner sleeve 1050. Inner sleeve 1050 may provide a substrate layer upon which first layer 1020 of elongate curved structural members may be formed. In addition, the inner surface of inner sleeve 1050 may be configured to mate with the surface of post 1008 of tibial plateau implant 1005. For example, the two surfaces may have textures or other features to prevent or otherwise minimize the likelihood that post 1008 comes out of central hole 1007.

Figure 11:
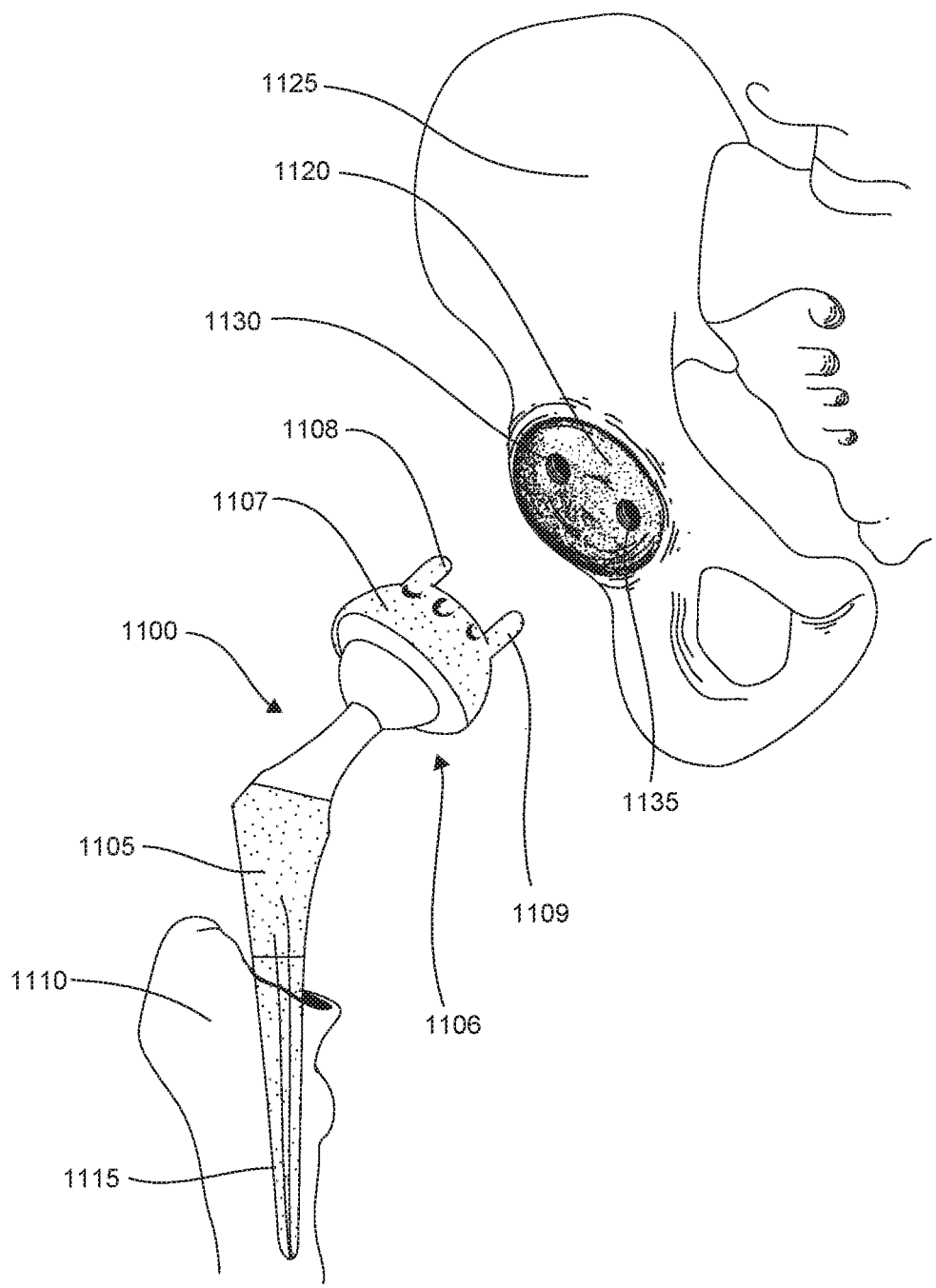
FIG. 11 is a schematic view of a hip replacement implant system according to an exemplary embodiment.

FIG. 11 is a schematic view of a hip replacement implant system according to an exemplary embodiment. As shown in FIG. 11, a hip replacement implant system 1100 may include a femoral component 1105 and pelvic component 1106. Femoral component 1105 may be configured for mounting onto the proximal end of a femur 1110. Femoral component 1105 may include a post 1115 configured to be inserted into a recess in femur 1110. The recess may include a portion of the medullary cavity within femur 1110, and may also be at least partially formed by the surgeon via cutting, drilling, reaming, or other bone shaping processes. Post 1115 may include a multi-layer bone interfacing lattice to facilitate maximum bone contacting surface within the recess of femur 1110. Stippling indicates general areas of post 1115 that may include a multi-layer bone interfacing lattice.

As shown in FIG. 11, pelvic component 1106 may be an acetabular cup configured for implantation in an acetabulum 1120 of a patient's pelvis 1125. Pelvic component 1106 may include a substantially spherical outer surface 1107. Outer surface 1107 may be configured to interface with acetabulum 1120. Pelvic component 1106 may be affixed to acetabulum 1120 with several mechanisms. For example, pelvic component 1106 may be affixed to acetabulum 1120 with one or more screws.

In addition, the screw fixation of pelvic component 1106 may be supplemented with bone ingrowth into outer surfaces of pelvic component 1106. For example, as shown in FIG. 11, in some embodiments, outer surface 1107 of pelvic component 1106 may include a multi-layer bone interfacing lattice similar to that described in other embodiments discussed herein. The multi-layer bone interfacing lattice of outer surface 1107 may promote bone ingrowth into outer surface 1107. Stippling indicates general areas of outer surface 1107 that may include a multi-layer bone interfacing lattice.

Additionally, in some embodiments, pelvic component 1106 may include one or more posts, such as a first post 1108 and a second post 1109. Upon implantation of pelvic component 1106, first post 1108 may be inserted into a first hole 1130, which may be drilled into acetabulum 1120. Similarly, upon implantation of pelvic component 1106, second post 1109 may be inserted into a second hole 1130, which may be drilled into acetabulum 1120. In some embodiments, first post 1108 and second post 1109 may have outer surfaces including a multi-layer bone interfacing lattice similar to that described in other embodiments discussed herein. The multi-layer bone interfacing lattice of first post 1108 and second post 1109 may promote bone ingrowth into the surfaces of these posts, and thus, provide additional fixation of pelvic component 1106 to pelvis 1125. Stippling indicates general areas of first post 1108 and second post 1109 that may include a multi-layer bone interfacing lattice.

Figure 12A:
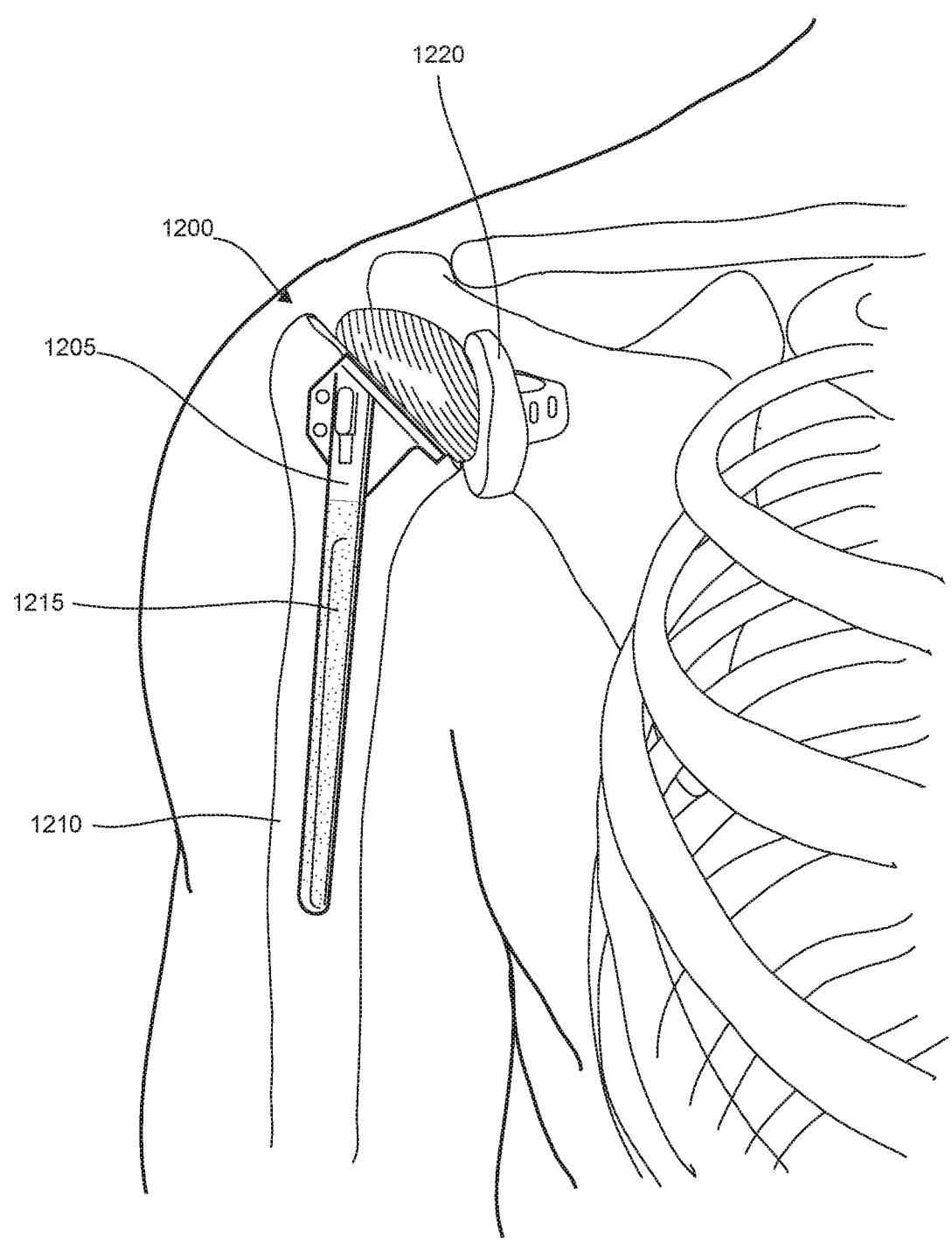
FIG. 12A is a schematic assembled view of a shoulder replacement implant system according to an exemplary embodiment.

FIG. 12A is a schematic view of a shoulder replacement implant system according to an exemplary embodiment. As shown in FIG. 12A, a shoulder replacement implant system 1200 may include a humoral component 1205 and a glenoid component 1220. Humoral component 1205 may be configured for mounting onto the proximal end of a humerus 1210. Humoral component 1205 may include a post 1215 configured to be inserted into a recess in humerus 1210. The recess may include a portion of the medullary cavity within humerus 1210, and may also be at least partially formed by the surgeon via cutting, drilling, reaming, or other bone shaping processes. Post 1215 may include a multi-layer bone interfacing lattice to facilitate maximum bone contacting surface within the recess of humerus 1210. Stippling indicates general areas of post 1215 that may include a multi-layer bone interfacing lattice.

Figure 12B:
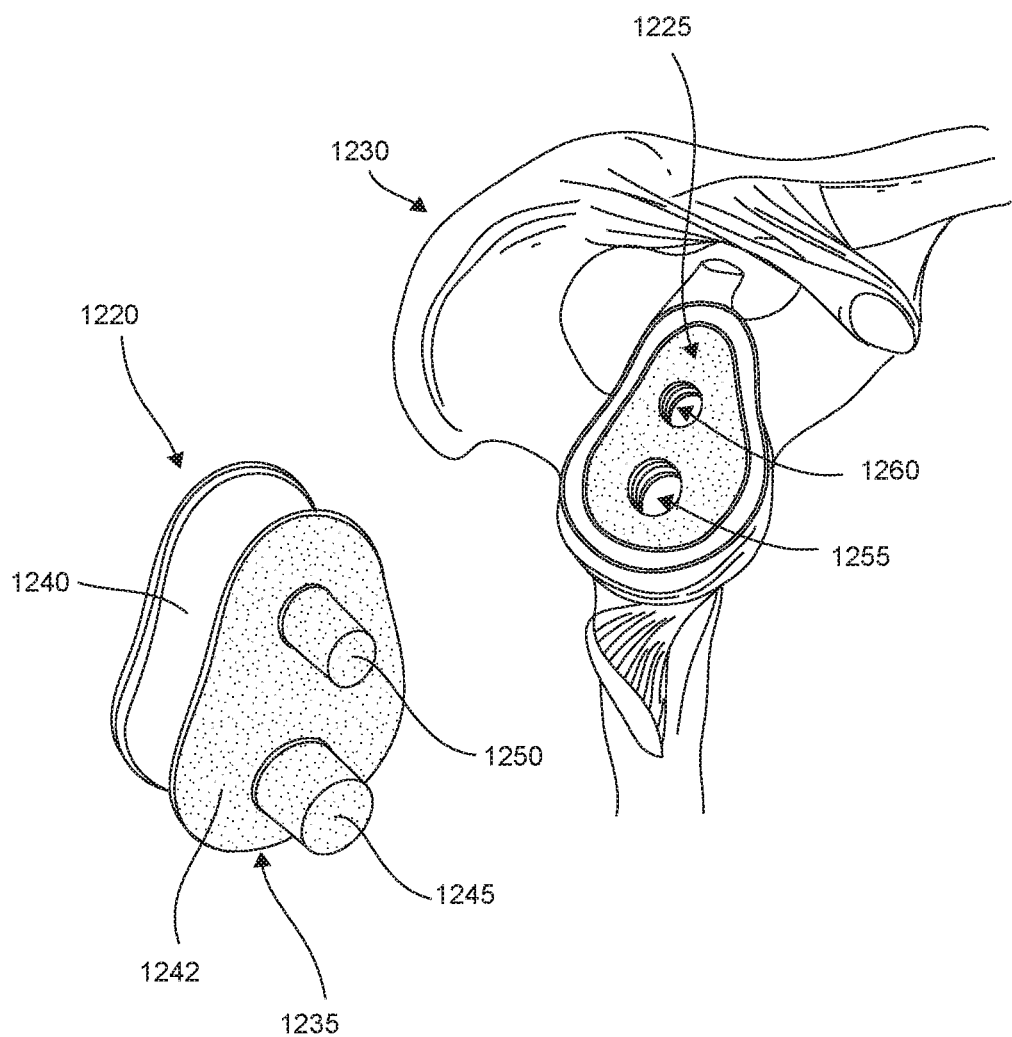
FIG. 12B is a schematic exploded view of a glenoid side of the shoulder replacement implant system shown in FIG. 12A.

FIG. 12B is a schematic exploded view of the glenoid side of the shoulder replacement implant system shown in FIG. 12A. Glenoid component 1220 may be configured to be implanted in glenoid cavity 1225 of a patient's shoulder 1230. Glenoid component 1220 may include a base component 1235 and a liner 1240. Liner 1240 may be a low friction material, such as plastic, which may facilitate motion against humeral component 1205 (see FIG. 12A). Liner 1240 may be attached to base component 1235, for example using a snap-in configuration.

Base component 1235 may be affixed within glenoid cavity 1225 with several mechanisms. For example, base component 1235 may be affixed within glenoid cavity 1225 by bone ingrowth into outer surfaces of base component 1235. For example, as shown in FIG. 12B, in some embodiments, a bone contacting surface 1242 of base component 1235 may include a multi-layer bone interfacing lattice similar to that described in other embodiments discussed herein. The multi-layer bone interfacing lattice of bone-contacting surface 1242 may promote bone ingrowth into outer surface 1242. Stippling indicates general areas of bone-contacting surface 1242 that may include a multi-layer bone interfacing lattice.

Additionally, in some embodiments, base component 1235 may include one or more posts, such as a first post 1245 and a second post 1250. Upon implantation of base component 1235, first post 1245 may be inserted into a first hole 1255, which may be drilled into glenoid cavity 1225. Similarly, upon implantation of base component 1235, second post 1250 may be inserted into a second hole 1260, which may be drilled into glenoid cavity 1225. In some embodiments, first post 1245 and second post 1250 may have outer surfaces including a multi-layer bone interfacing lattice similar to that described in other embodiments discussed herein. The multi-layer bone interfacing lattice of first post 1245 and second post 1250 may promote bone ingrowth into the surfaces of these posts, and thus, provide additional fixation of base component 1235 to glenoid cavity 1225. Stippling indicates general areas of first post 1245 and second post 1250 that may include a multi-layer bone interfacing lattice.

Figure 13:
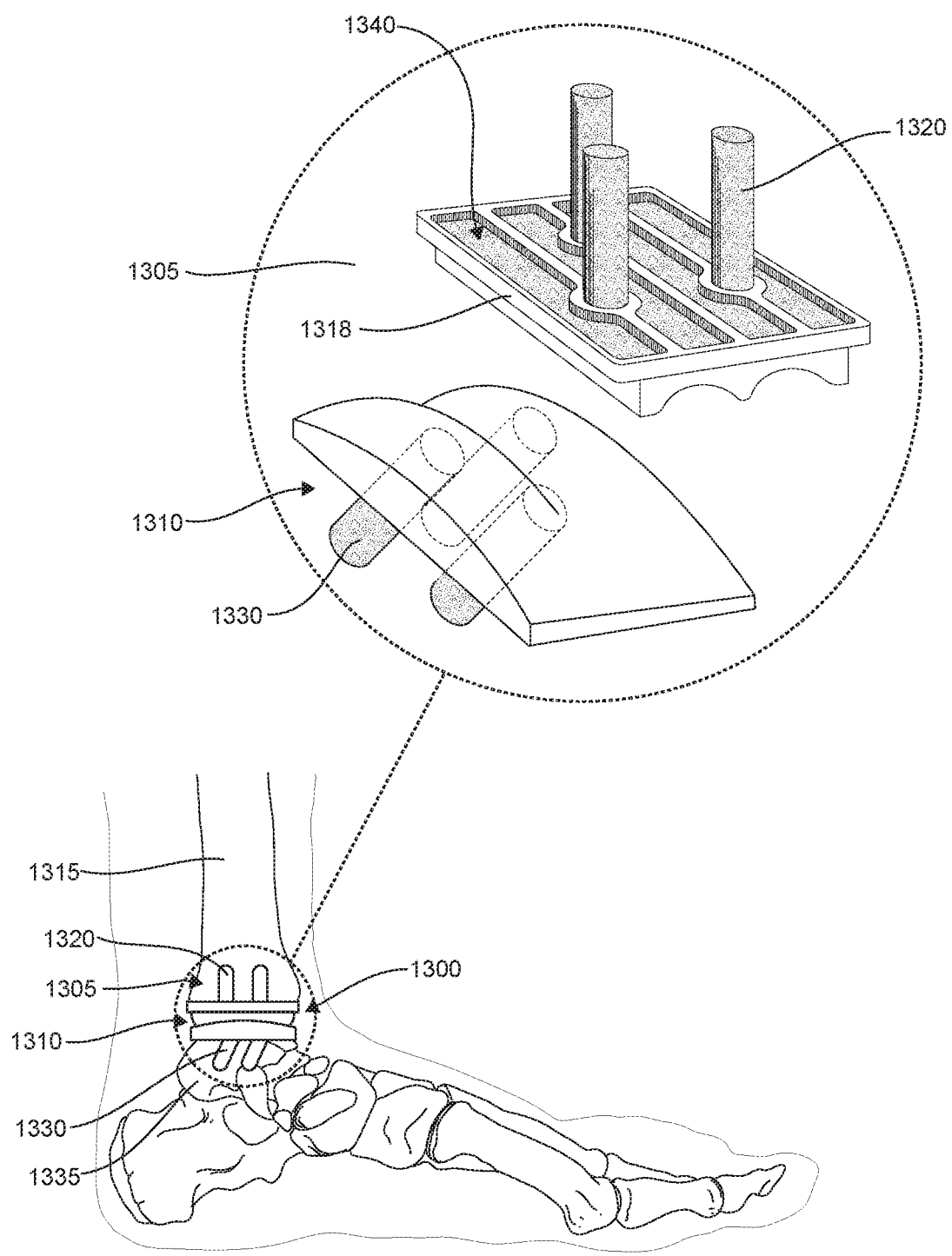
FIG. 13 is a schematic assembled view of an ankle replacement implant system according to an exemplary embodiment.

FIG. 13 is a schematic assembled view of an ankle replacement implant system according to an exemplary embodiment. There are multiple components of an ankle replacement system that can implement a multi-layer bone interfacing lattice. As shown in FIG. 13, an ankle replacement implant system 1300 may include a tibial component 1305 and a talar component 1310. Tibial component 1305 may be configured for mounting onto the distal end of a tibia 1315. Tibial component 1305 may include a baseplate 1318 and one or more posts 1320 extending from baseplate 1318 and configured to be inserted into one or more recesses in tibia 1315. The recesses in tibia 1315 may include a portion of the medullary cavity within the tibia, and may also be at least partially formed by the surgeon via cutting, drilling, reaming, or other bone shaping processes. Posts 1320 may include a multi-layer bone interfacing lattice to facilitate maximum bone contacting surface within the recesses. Stippling indicates general areas of posts 1320 that may include a multi-layer bone interfacing lattice.

Baseplate 1318 may include a bone contacting surface having one or more recesses 1340. Recesses 1340 may be at least partially filled with a multi-layer bone interfacing lattice to promote bone ingrowth.

Talar component 1310 may also include one or more posts 1330 configured for insertion into one or more recesses in the proximal end of a talus 1335. The one or more recesses may be at least partially formed by the surgeon via cutting, drilling, reaming, or other bone shaping processes. Posts 1330 may also include a multi-layer bone interfacing lattice to facilitate maximum bone contacting surface within the recess. Stippling indicates general areas of posts 1330 that may include a multi-layer bone interfacing lattice.

Figure 14:
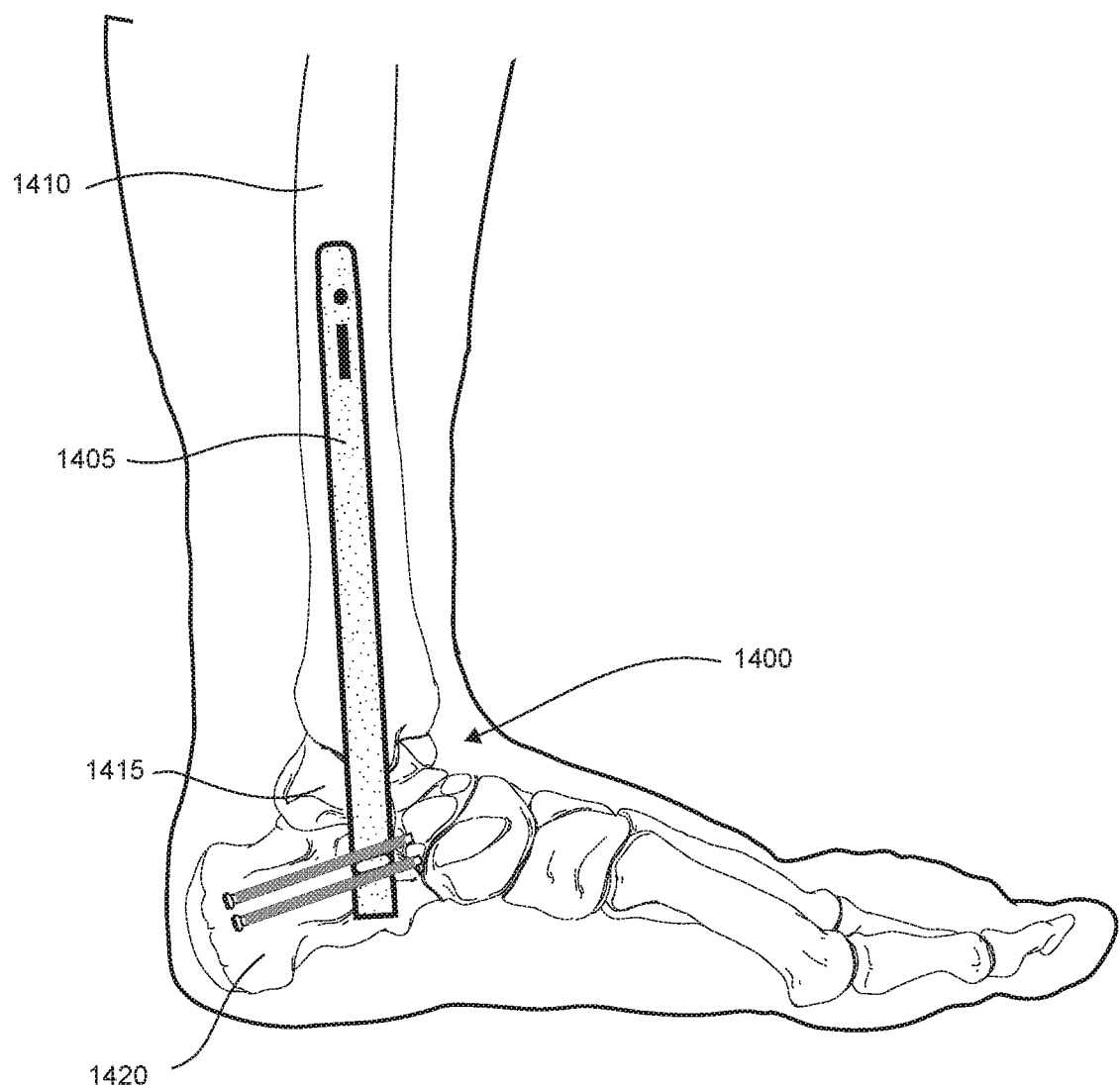
FIG. 14 is a schematic assembled view of an ankle fusion implant system according to an exemplary embodiment.

FIG. 14 is a schematic assembled view of an ankle fusion implant system according to an exemplary embodiment. As shown in FIG. 14, an ankle fusion implant system 1400 may include an intramedullary rod 1405. Intramedullary rod 1405 may be configured for mounting onto the distal end of a tibia 1410. As shown in FIG. 14, intramedullary rod 1405 may also be inserted through a talus 1415 and a calcaneus 1420. Intramedullary rod 1405 may be inserted within a recess in tibia 1410 that may include a portion of the medullary cavity within tibia 1410. In addition, intramedullary rod 1405 may be inserted into recesses in talus 1415 and calcaneus 1420 that may be at least partially formed by the surgeon via cutting, drilling, reaming, or other bone shaping processes.

Intramedullary rod 1405 may include a multi-layer bone interfacing lattice to facilitate maximum bone contacting surface within the recesses within the tibia and ankle bones. Stippling indicates general areas of intramedullary rod 1405 that may include a multi-layer bone interfacing lattice.

Figure 15:
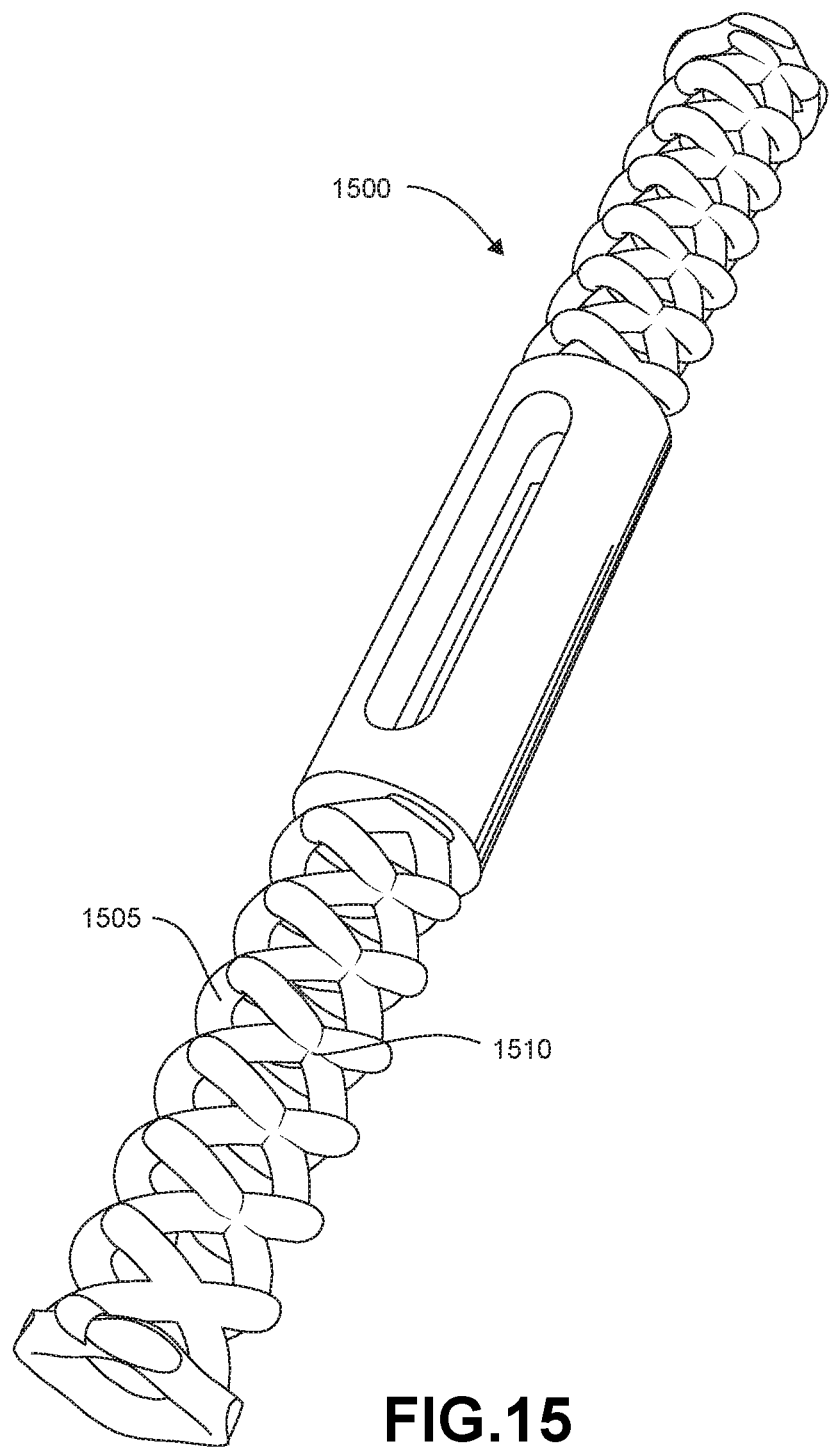
FIG. 15 is a schematic perspective view of an alternative intramedullary rod embodiment for an ankle fusion implant system.

FIG. 15 is a schematic perspective view of an alternative intramedullary rod embodiment for an ankle fusion implant system. FIG. 15 shows an intramedullary rod 1500. Intramedullary rod 1500 may include a plurality of elongate curved structural members 1505. As shown in FIG. 15, structural members 1505 may intersect at junctions 1510 that are recessed from the outermost envelope of intramedullary rod 1500. Accordingly, the support member junctions are generally not located at the bone-implant interface when rod 1500 is implanted.

Figure 16:
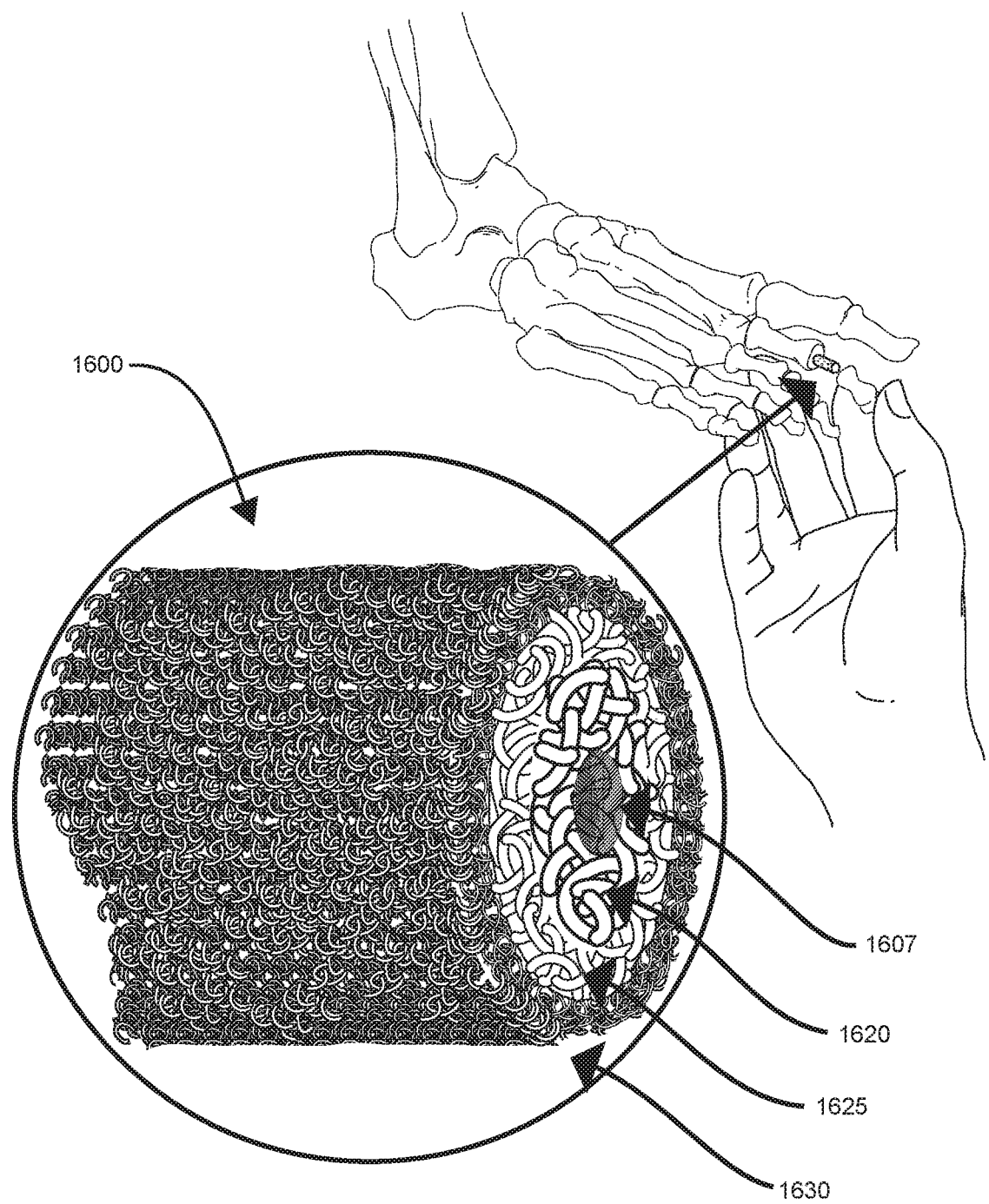
FIG. 16 is a schematic view of a hammertoe correction implant according to an exemplary embodiment.

FIG. 16 is a schematic view of a hammertoe correction implant according to an exemplary embodiment. As shown in FIG. 16, a hammertoe correction implant 1600 may be implanted into adjacent phalanges to fuse an interphalangeal joint. The outer surface of implant 1600 may include a multi-layer bone interfacing lattice of elongate curved structural members to facilitate bone ingrowth. For example, as shown in FIG. 16, implant 1600 may include a first layer 1620, a second layer 1625, and a third layer 1630. In some embodiments, implant 160 may have a central hole 1607. Bone graft material may be placed in central hole 1607 to facilitate fixation and bone ingrowth.

FIG. 16 depicts a substantially cylindrical embodiment having a three layer lattice. This configuration may be used for any of a number of different intramedullary rods. In some embodiments, such cylindrical implants may be used to join adjacent bones, such as phalanges in the foot (as shown in FIG. 16) or the hand. In other cases, such implants may be used to repair long bones, such as the humerus, femur, tibia, and other such bones. For severe breaks, long bones may be repaired by placing a rod inside the substantially hollow bone. The three layer lattice discussed herein may facilitate fixation and bone ingrowth for such intramedullary rods.

In addition, other intramedullary implants are also possible. For example, in some embodiments, an implant having dual, concentric helical members may be utilized.

Figure 17:
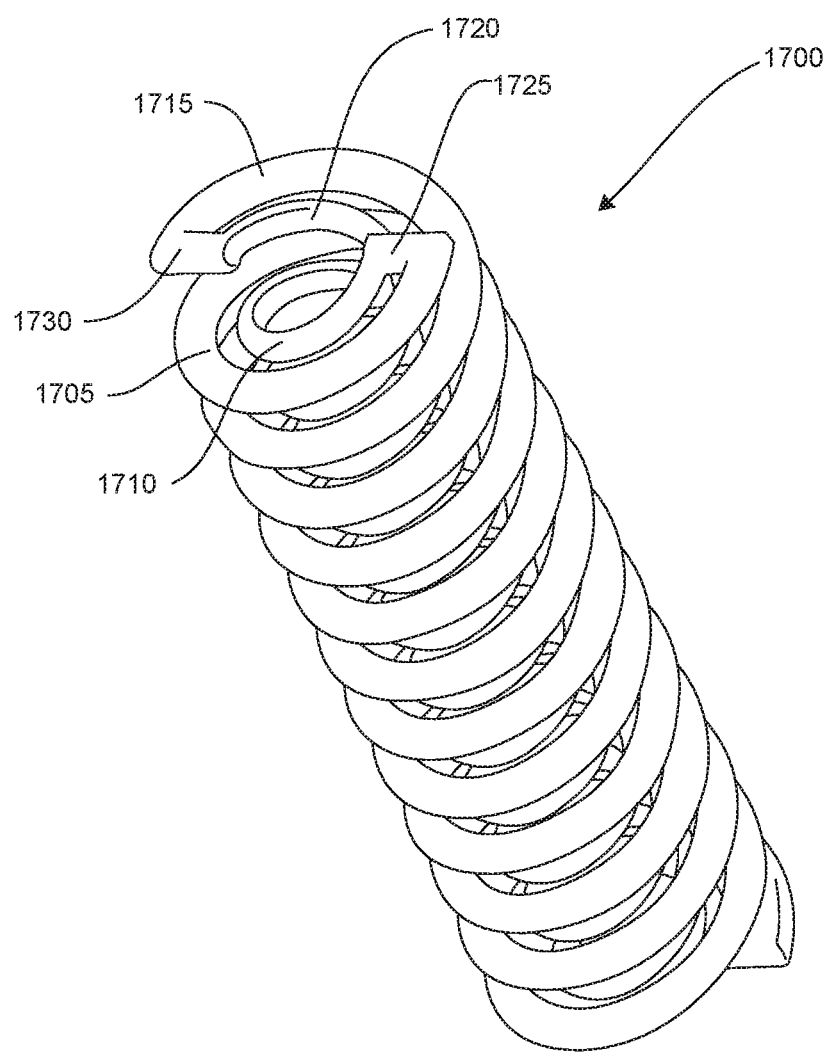
FIG. 17 is a schematic perspective view of another substantially cylindrical implant configured for intramedullary implantation.

FIG. 17 is a schematic perspective view of another substantially cylindrical implant configured for intramedullary implantation. As shown in FIG. 17, an implant 1700 may include a first outer spiral 1705 and first inner spiral 1710. In addition, implant 1700 may include a second outer spiral 1715 and a second inner spiral 1720. This dual, concentric spiral configuration may provide structural support, while maintaining a substantially hollow inner volume to receive bone graft material and/or bone ingrowth.

The inner and outer spirals may have separate starting points akin to a dual-start thread. In addition, the inner and outer spirals may be joined to one another at the ends. For example, as shown in FIG. 17, first outer spiral 1705 and first inner spiral 1710 may be joined by a first connecting portion 1725. As also shown in FIG. 17, second outer spiral 1715 and second inner spiral 1720 may be joined by a second connecting portion 1730.

Figure 18:
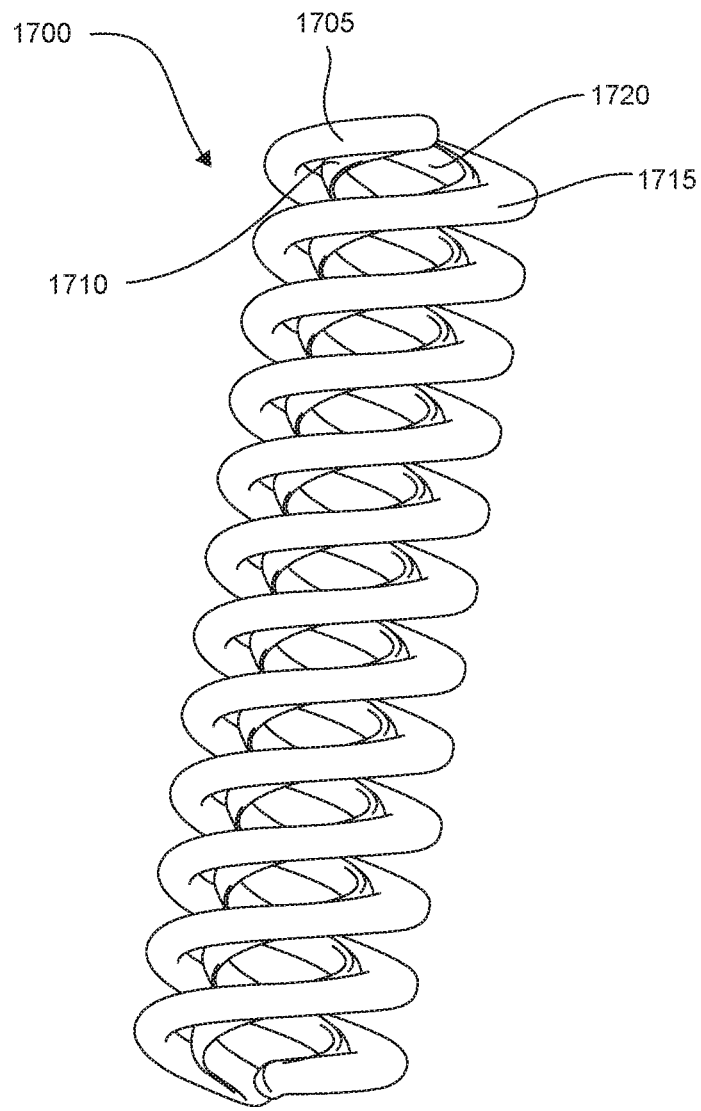
FIG. 18 is another schematic perspective view of the implant shown in FIG. 17.
Figure 19:
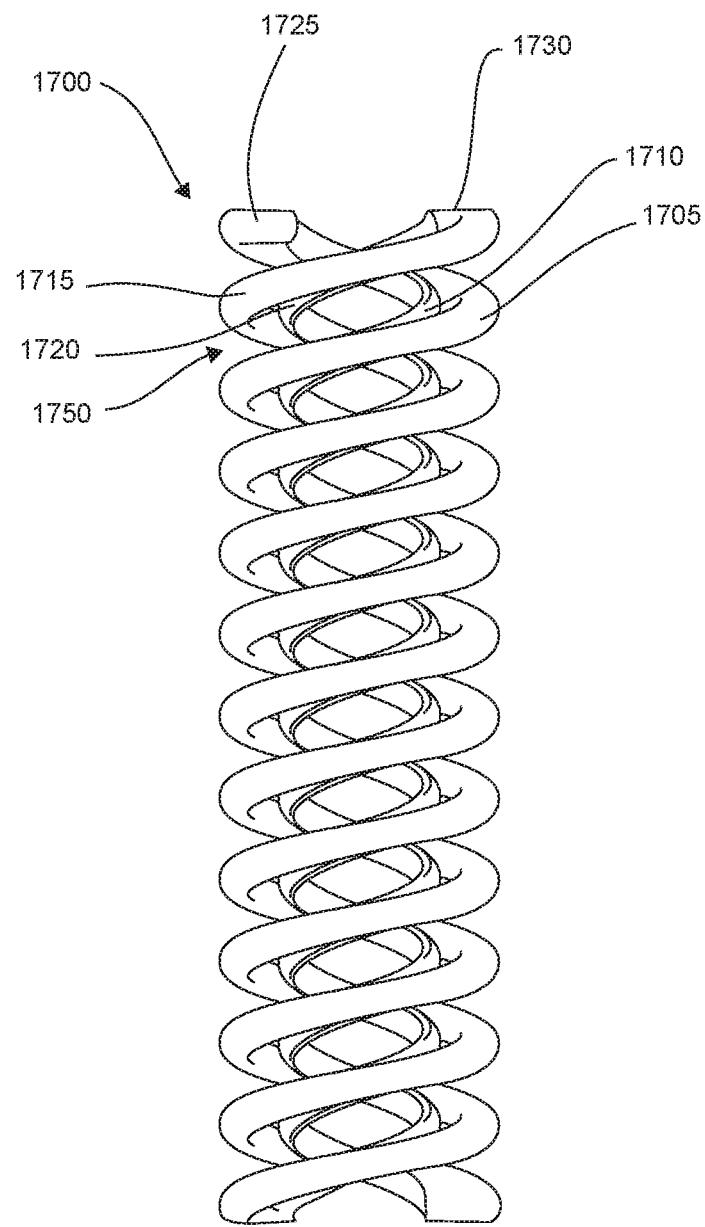
FIG. 19 is a schematic lateral view of the implant shown in FIG. 17.
Figure 20:
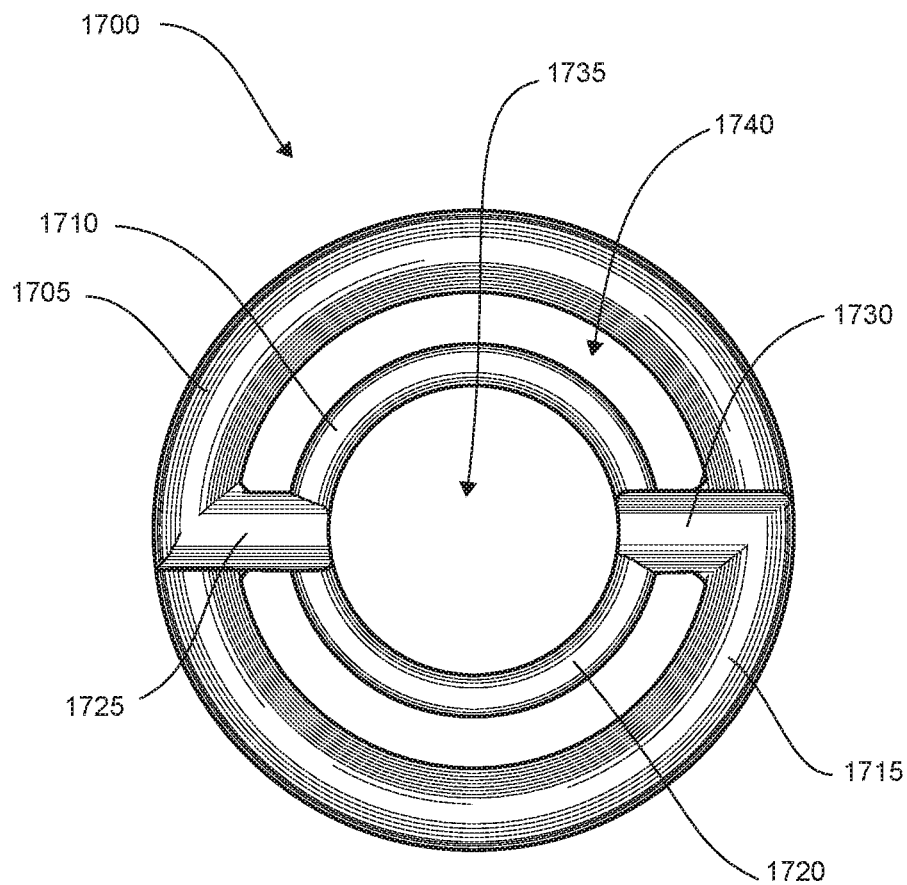
FIG. 20 is a schematic end view of the implant shown in FIG. 17.

FIGS. 18-20 illustrate other views of implant 1700. As shown in FIG. 19, longitudinal spacing 1750 may be provided between spirals. Ain addition, as shown in FIG. 20, the outer and inner spirals may be concentric. In addition, first inner spiral 1710 and second inner spiral 1720 may define a cylindrical central opening 1735. In addition, the inner spirals and outer spirals may define an annular space 1740 between the inner spirals and the outer spirals. Central opening 1735, annular space 1740, and longitudinal spacing 1750 may be configured to receive bone graft material and/or bone ingrowth.

Figure 21:
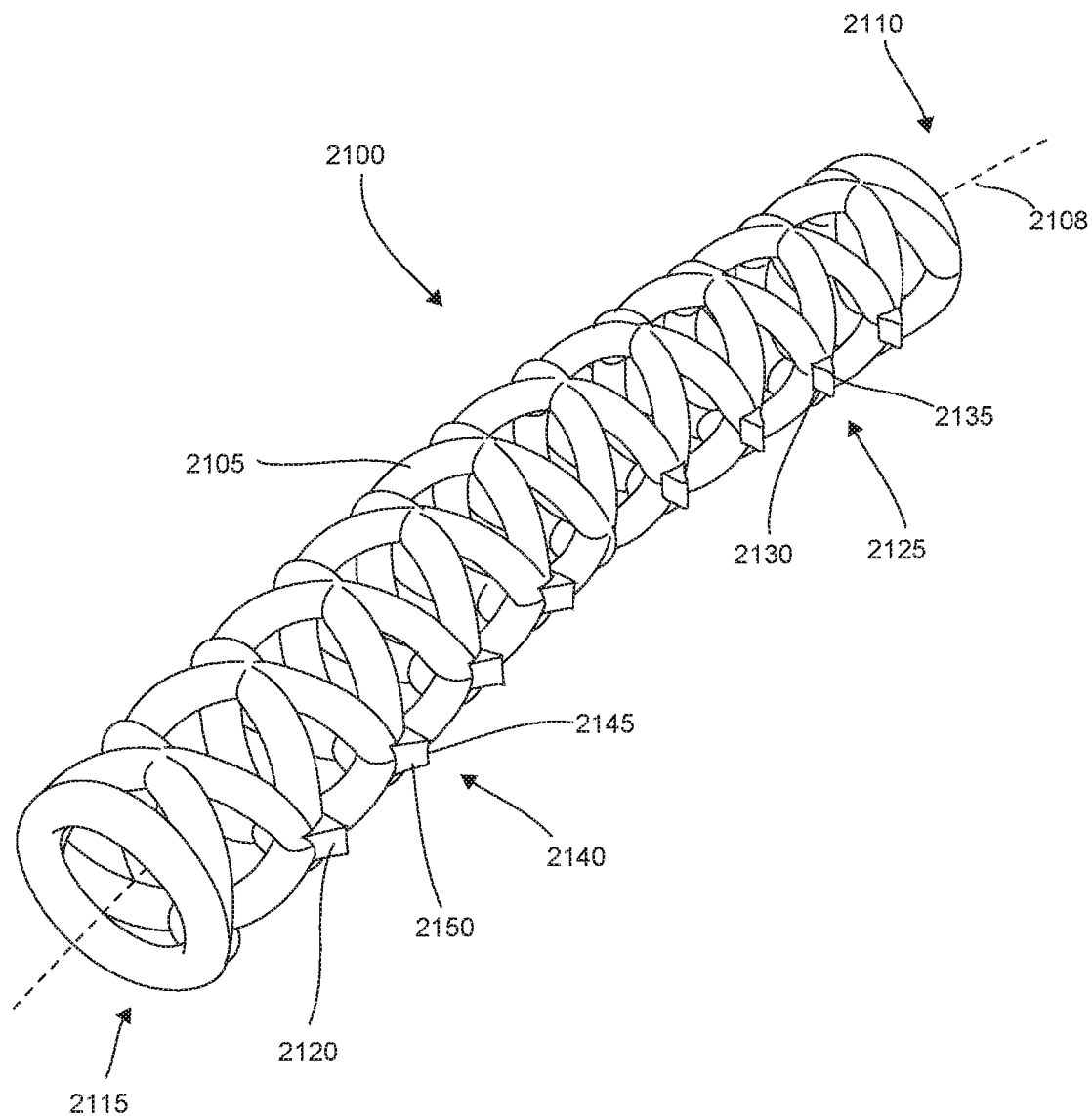
FIG. 21 is a schematic perspective view of a substantially cylindrical intramedullary implant according to another exemplary embodiment.

FIG. 21 is a schematic perspective view of a substantially cylindrical intramedullary implant according to another exemplary embodiment. FIG. 21 shows an implant 2100 being formed of a plurality of criss-crossing support members 2105 forming a substantially cylindrical grid or cage having a longitudinal axis 2108. As shown in FIG. 21, implant 2100 may have a bend in it, such that longitudinal axis 2108 has a curved portion. This bend may facilitate implantation into separate pieces of bone that are intended to be maintained at an angle with respect to one another.

Implant 2100 may be configured to be placed within elongate bones, such as phalanges of the hand or foot. In some cases, implant 2100 may be configured to be implanted in the intramedullary space of larger bones, such as the femur or humerus. In some embodiments a first end 2110 of implant 2100 may be inserted into a first bone or first piece of bone, and a second end 2115 of implant 2100 may be inserted into a separate bone or piece of bone. By inserting opposing ends of implant 2100 into separate bones (e.g., phalanges) or pieces of bones (e.g., broken long bones), implant 2100 may stabilize these bones to facilitate fusion of separate bones or healing of separate broken bone pieces.

In order to prevent egress of implant 2100 after implantation, implant 2100 may include one or more spikes 2120. Spikes 2120 may be configured to facilitate insertion of implant 2100 but prevent removal of implant 2100 as well as preventing rotation of implant 2100 about longitudinal axis 2108. For example, implant may include a first spike 2125 located proximate first end 2110 of implant 2100. First spike 2125 may include a first surface 2130 facing away from first end 2110 and extending substantially perpendicularly with respect to longitudinal axis 2108. First spike 2125 may also include a second surface 2135 facing toward first end 2110 of implant 2100 and extending at a non-zero angle with respect to longitudinal axis 2108. That is, as second surface 2135 extends away from the surface of support members 2105, second surface 2135 slopes away from first end 2110 of implant 2100. The slope of second surface 2135 may facilitate insertion of implant 2100 and the perpendicular configuration of first surface 2130 may prevent removal of implant 2100 from within a bone into which it has been implanted.

As shown in FIG. 21, spikes 2120 at opposing ends of implant 2100 may have sloped surfaces facing in opposite directions. That is, the spikes closest to first end 2110 may have sloped surfaces facing toward first end 2110, as with first spike 2125. And the spikes closest to second end 2115 may have sloped surfaces facing toward second end 2115. For example, implant may include a second spike 2140 proximate to second end 2115 of implant 2100. Second spike 2140 may include a first surface 2145 facing away from second end 2115 and extending substantially perpendicularly from longitudinal axis 2108. In addition, second spike 2140 may include a second surface 2150 facing toward second end 2115 and extending at a non-zero angle with respect to longitudinal axis 2108.

Figure 22:
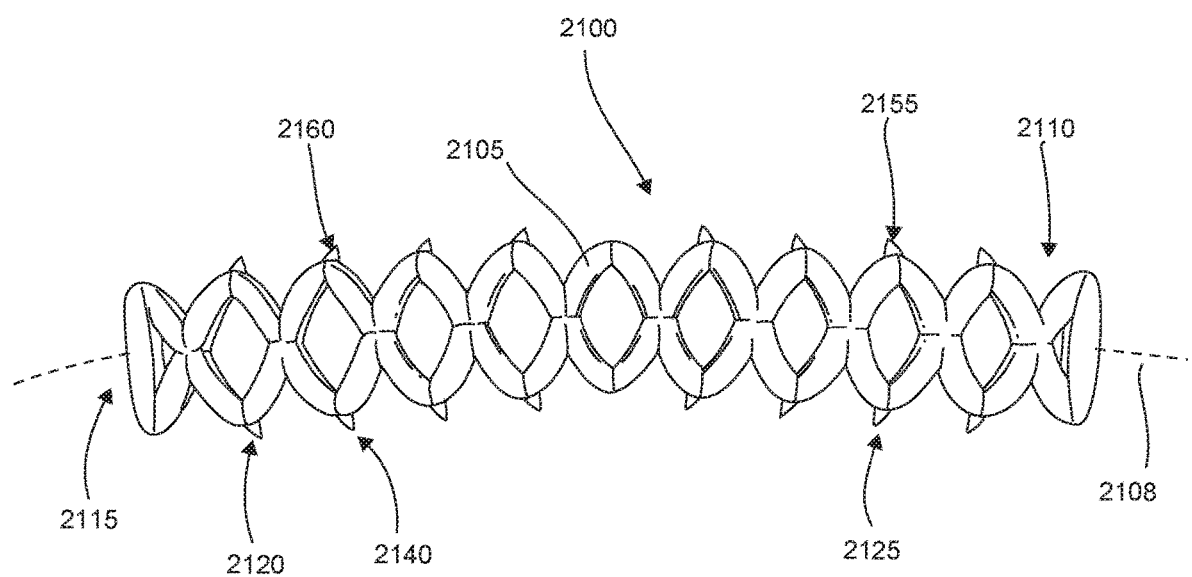
FIG. 22 is a schematic lateral view of the implant shown in FIG. 21.

FIG. 22 is a schematic lateral view of the implant shown in FIG. 21. As shown in FIG. 22, in some embodiments, spikes 2120 may be disposed on opposing sides of implant 2100. For example, implant 2100 may include a third spike 2155 disposed opposite first spike 2125. Similarly, implant 2100 may include a fourth spike 2160 disposed opposite second spike 2140. Accordingly, in at least one plane, implant 2100 may be substantially symmetrical about longitudinal axis 2108.

Figure 23:
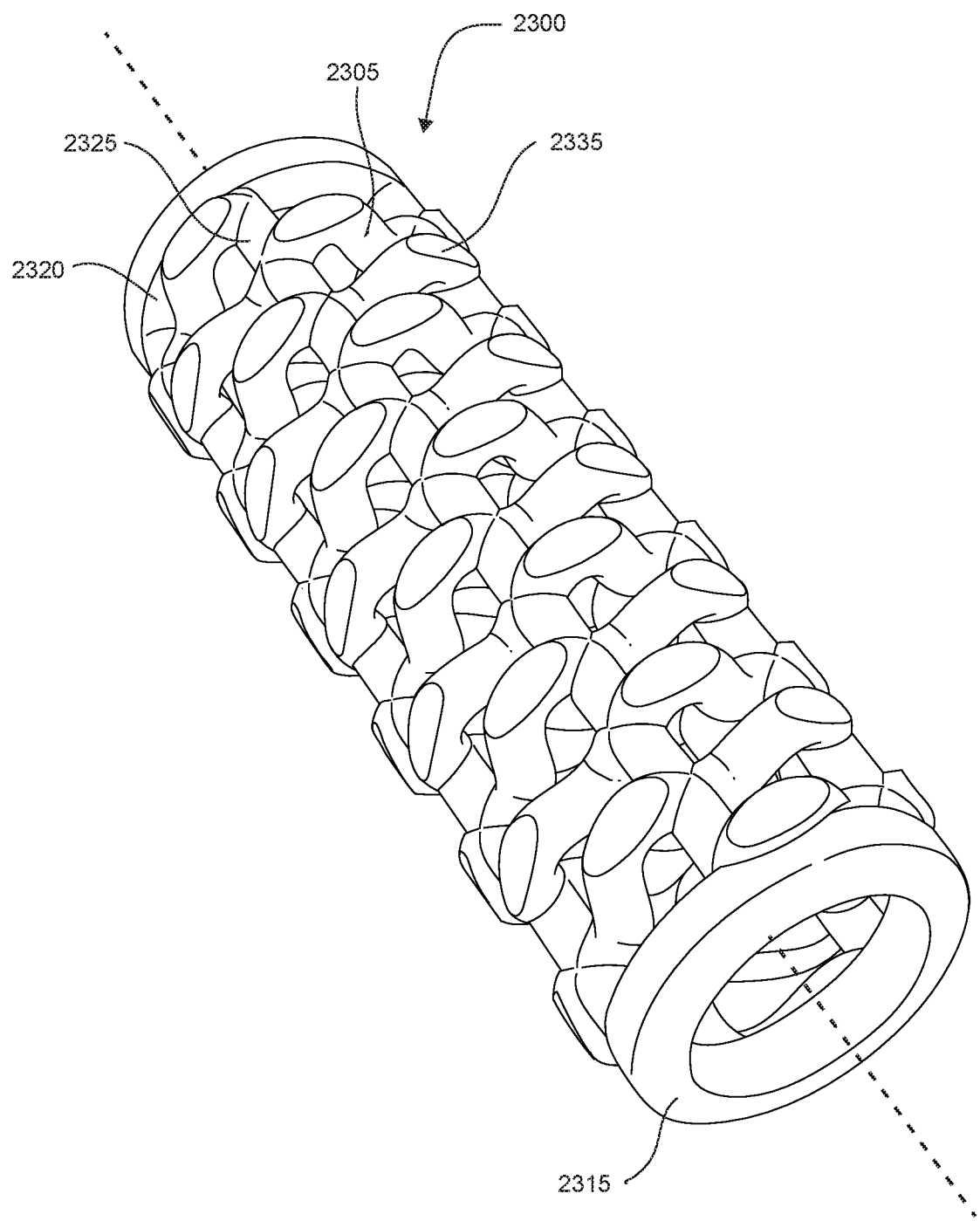
FIG. 23 is a schematic perspective view of a substantially cylindrical intramedullary implant according to another exemplary embodiment.

FIG. 23 is a schematic perspective view of a substantially cylindrical intramedullary implant according to another exemplary embodiment. As shown in FIG. 23, an implant 2300 may be formed of a plurality of spiral members 2305 extending about a central longitudinal axis 2310. To support spiral members 2305, implant 2300 may include a framework. The framework may be formed from a first substantially circular end member 2315 and a second substantially circular end member 2320. A plurality of longitudinal members 2325 may extend between first substantially circular end member 2315 and second substantially circular end member 2320. Spiral members 2305 may be supported by longitudinal members 2325. Implant 2300 may have any suitable longitudinal length and radial diameter with respect to longitudinal axis 2310. For example, implant 2300 may have a suitable size for implantation within small bones like phalanges or large bones such as the humerus or femur.

As illustrated in FIG. 23, spiral members 2305 may have a substantially sinusoidal configuration, deviating in and out radially with respect to longitudinal axis 2310. In addition, spiral members 2305 may include a plurality of flattened surfaces 2335 that collectively form at least a portion of the outer surface of implant 2300. The structural members of implant 2300 define a central hollow cavity in the interior of implant 2300. The central hollow cavity may be configured to receive bone graft material.

Figure 24:
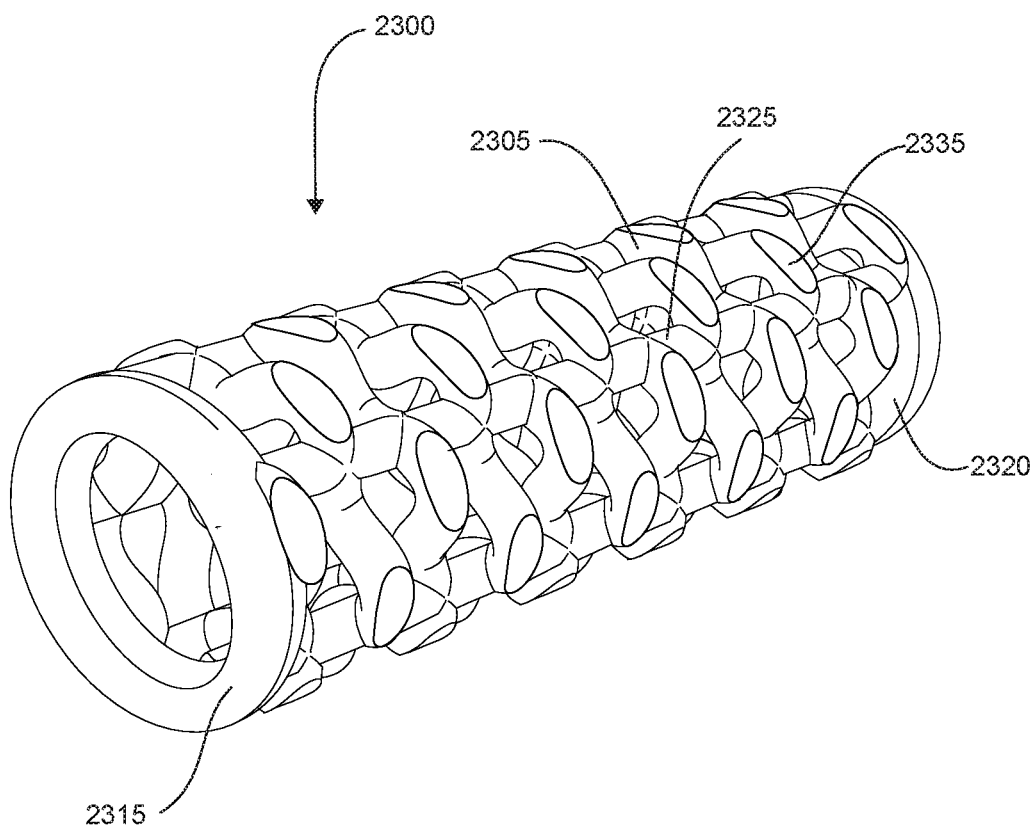
FIG. 24 is another schematic perspective view of the implant shown in FIG. 23.

FIG. 24 is another schematic perspective view of the implant shown in FIG. 23. FIG. 24 better shows the central hollow cavity, as well as the sinusoidal configuration of spiral members 2305, as seen from the inside of implant 2300.

Figure 25:
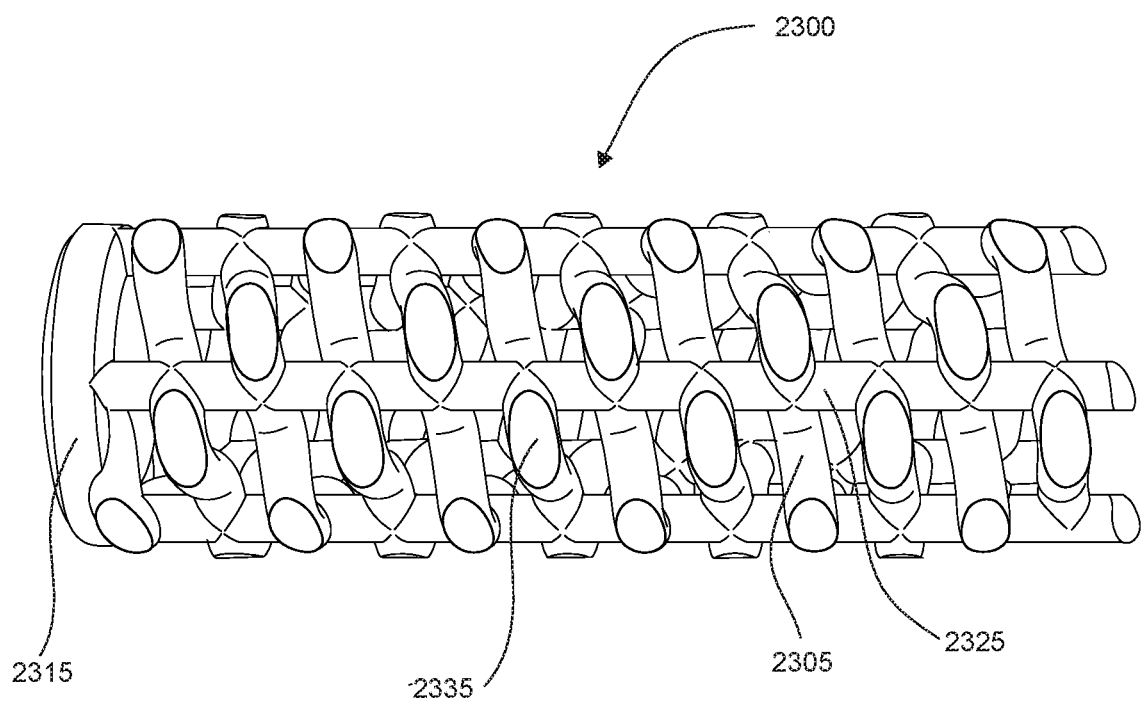
FIG. 25 is a schematic lateral view of the implant shown in FIG. 23.

FIG. 25 is a schematic lateral view of the implant shown in FIG. 23. FIG. 25 illustrates the angle or pitch of spiral members 2305. FIG. 25 also shows that flattened surfaces 2335 of spiral members 2305 alternate as to which side of longitudinal members 2325 they are disposed. This may provide an even distribution of surface area for the outer (bone contacting) surface of implant 2300.

The various components of an implant may be fabricated from biocompatible materials suitable for implantation in a human body, including but not limited to, metals (e.g. titanium or other metals), synthetic polymers, ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g. γTitanium Aluminides, $Ti_6$—$Al_4$—V ELI (ASTM F 136 and F 3001), or $Ti_6$—$Al_4$—V (ASTM F 2989, F 1108 and ASTM F 1472)) and inert, biocompatible polymers, such as polyether ether ketone (PEEK) (e.g. PEEK-OPTIMA®, Invibio Inc and Zeniva Solvay Inc.). Optionally, the implant contains a radiopaque marker to facilitate visualization during imaging.

In different embodiments, processes for making an implant can vary. In some embodiments, the entire implant may be manufactured and assembled via readditional/CNC machining, injection-molding, casting, insert-molding, co-extrusion, pultrusion, transfer molding, overmolding, compression molding, 3-Dimensional (3-D) printing (including Direct Metal Laser Sintering and Electron Beam Melting), dip-coating, spray-coating, powder-coating, porous-coating, milling from a solid stock material and their combinations. Moreover, the embodiments can make use of any of the features, parts, assemblies, processes and/or methods disclosed in the "The Coiled Implant Application."

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. An implant, comprising:
a body including a substrate and a bone interfacing lattice disposed on the substrate;
wherein the bone interfacing lattice includes at least two layers of elongate curved structural members;
wherein the at least two layers of elongate curved structural members include a first layer adjacent the substrate and configured to receive bone ingrowth and a second layer adjacent the first layer and configured to receive bone ingrowth;
wherein the first layer has a first deformability and the second layer has a second deformability;
wherein the second deformability is greater than the first deformability such that the second layer has a compressibility that renders it configured to conform to irregularities in a recess within a bone; and
wherein an interface between the first layer and the second layer is a transition region having a thickness within which the elongate curved structural members of the first layer are intertwined with the elongate curved structural members of the second layer; and
wherein the first deformability is a plastic deformability and the second deformability is a plastic deformability.

2. The implant of claim 1, wherein the first layer has a first thickness that is substantially consistent such that an outer shape of the first layer is substantially the same as an outer shape of the substrate.

3. The implant of claim 2, wherein the second layer has a second thickness that is substantially consistent such that an outer shape of the second layer is substantially the same as the outer shape of the first layer.

4. The implant of claim 1, wherein the elongate curved structural members of the first layer have a first gauge and the elongate curved structural members of the second layer have a second gauge.

5. The implant of claim 4 wherein the second gauge is less than the first gauge.

6. The implant of claim 1, wherein the bone interfacing lattice includes a third layer of elongate curved structural members adjacent the second layer; and
wherein the third layer has a third deformability that is greater than the second deformability of the second layer of elongate curved structural members.

7. The implant of claim 1, wherein the body has a substantially elongate shape configured to be inserted into a recess in a bone.

8. The implant of claim 1, wherein one or more of the elongate curved structural members have a spiraling geometry.

9. An implant, comprising:
a body including a substrate and a bone interfacing lattice disposed on the substrate;
wherein the bone interfacing lattice includes at least two layers of elongate curved structural members;
wherein the at least two layers of elongate curved structural members includes a first layer adjacent the substrate and configured to receive bone ingrowth and a second layer adjacent the first layer and configured to receive bone ingrowth;
wherein the elongate curved structural members of the first layer have a first gauge and the elongate curved structural members of the second layer have a second gauge;
wherein the second gauge is less than the first gauge such that the second layer has a compressibility that renders it configured to conform to irregularities in a recess within a bone; and
wherein an interface between the first layer and the second layer is a transition region having a thickness within which the elongate curved structural members of the first layer are intertwined with the elongate curved structural members of the second layer; and
wherein the first deformability is a plastic deformability and the second deformability is a plastic deformability.

10. The implant of claim 9, wherein the first layer has a first thickness that is substantially consistent such that an outer shape of the first layer is substantially the same as an outer shape of the substrate.

11. The implant of claim 10, wherein the second layer has a second thickness that is substantially consistent such that an outer shape of the second layer is substantially the same as the outer shape of the first layer.

12. The implant of claim 9, wherein one or more of the elongate curved structural members have a spiraling geometry.

* * * * *